(12) United States Patent
Fletcher

(10) Patent No.: US 12,120,998 B2
(45) Date of Patent: Oct. 22, 2024

(54) CANNABIS VARIETY WHICH PRODUCES GREATER THAN 50% FEMALE PLANTS

(71) Applicant: NEW WEST GENETICS INC., Fort Collins, CO (US)

(72) Inventor: Richard S. Fletcher, Fort Collins, CO (US)

(73) Assignee: NEW WEST GENETICS INC., Fort Collins, CO (US)

( * ) Notice: Subject to any disclaimer, the term of this patent is extended or adjusted under 35 U.S.C. 154(b) by 696 days.

(21) Appl. No.: 17/250,303

(22) PCT Filed: Jul. 2, 2019

(86) PCT No.: PCT/US2019/040332
§ 371 (c)(1),
(2) Date: Dec. 30, 2020

(87) PCT Pub. No.: WO2020/010102
PCT Pub. Date: Jan. 9, 2020

(65) Prior Publication Data
US 2021/0144947 A1  May 20, 2021

Related U.S. Application Data

(60) Provisional application No. 62/693,538, filed on Jul. 3, 2018.

(51) Int. Cl.
| | |
|---|---|
| *A01H 6/28* | (2018.01) |
| *A01H 1/02* | (2006.01) |
| *A01H 1/04* | (2006.01) |
| *A01H 5/02* | (2018.01) |
| *C12Q 1/6895* | (2018.01) |

(52) U.S. Cl.
CPC ............... *A01H 6/28* (2018.05); *A01H 1/022* (2021.01); *A01H 1/045* (2021.01); *A01H 5/02* (2013.01); *C12Q 1/6895* (2013.01); *C12Q 2600/13* (2013.01); *C12Q 2600/158* (2013.01)

(58) Field of Classification Search
None
See application file for complete search history.

(56) References Cited

U.S. PATENT DOCUMENTS

| | | |
|---|---|---|
| 2010/0031382 A1 | 2/2010 | Baerends |
| 2016/0177404 A1 | 6/2016 | McKernan |

FOREIGN PATENT DOCUMENTS

| | | |
|---|---|---|
| CN | 104604502 A | 5/2015 |
| WO | 2014145490 A2 | 9/2014 |
| WO | 2014145490 A3 | 9/2014 |

OTHER PUBLICATIONS

Hall et al., Review of Flowering Control in Industrial Hemp, 2012, Journal of Natural Fibers 9: 23-36 (Year: 2012).*
Hall et all 2012, Journal of Natural Fibers 9: 23-36 (Year: 2012).*
Bowen et al., "Therapeutic benefit of Smoked cannabis in randomized Placebo-Controlled Studies", Pharmacotherapy, vol. 38, No. 1, pp. 80-85, 2018.
International Searching Authority in connection with PCT/US2019/040332 filed Jul. 2, 2019, "The International Search Report and the Written Opinion of the international Searching Authority, or the Declaration", 14 pages, mailed Nov. 26, 2019.
Faux et al., "Identification of QTLs for sex expression in dioecious and monoecious hemp (*Cannabis sativa* L.)", Euphytica, vol. 209, pp. 357-376, 2016.
Hall et al., "Review of Flowering Control in Industrial Hemp", Journal of Natural Fibers, vol. 9, pp. 23-36, 2012.
Razumova et al., "Molecular cytogenetic analysis of monoecious hemp (*Cannabis sativa* L.) cultivars reveals its karyotype variations and sex chromosomes constitution", Protoplasma, vol. 253, pp. 895-901, 2016.

* cited by examiner

*Primary Examiner* — Mykola V. Kovalenko
*Assistant Examiner* — Aleksandar Radosavljevic
(74) *Attorney, Agent, or Firm* — McKee, Voorhees & Sease, PLC

(57) ABSTRACT

According to the invention, there is provided a novel hemp *Cannabis* cultivar which produces a skewed ratio of female plants. This invention thus relates to the seeds of hemp *Cannabis* cultivar of the invention, to the plants of hemp *Cannabis* cultivar of the invention, to plant parts of hemp *Cannabis* cultivar of the invention, to methods for producing a *Cannabis* cultivar by crossing the hemp *Cannabis* cultivar of the invention with another *Cannabis* cultivar, and to methods for producing a *Cannabis* cultivar containing in its genetic material one or more backcross conversion traits or transgenes and to the backcross conversion *Cannabis* plants and plant parts produced by those methods.

5 Claims, No Drawings

Specification includes a Sequence Listing.

CANNABIS VARIETY WHICH PRODUCES GREATER THAN 50% FEMALE PLANTS

CROSS-REFERENCE TO RELATED APPLICATIONS

This application claims priority to provisional application U.S. Ser. No. 62/693,538, filed Jul. 3, 2018, which is incorporated herein by reference in its entirety.

FIELD OF THE INVENTION

The present invention relates to the field of plant breeding. In particular, this invention relates to specialty *Cannabis* plants, cultivars and varieties, including methods for making and using said *Cannabis* plants and compositions derived thereof.

BACKGROUND OF THE INVENTION

Industrial hemp is legally defined in the United States as *Cannabis* which contains 0.3% or less total sample dry weight of Δ9-Tetrahydrocannabinal (THC). THC content is normally well above the 0.30% threshold in modern varieties of *Cannabis*. THC is one of an estimated 85 cannabinoids (a class of terpenoids) synthesized in *Cannabis* species (El-Alfy et al., 2010, "Antidepressant-like effect of delta-9-tetrahydrocannabinol and other cannabinoids isolated from *Cannabis sativa* L", Pharmacology Biochemistry and Behavior 95 (4): 434-42).

Endogenous cannabinoid receptors located throughout the human body are known to be binding sites for cannabinoids (Kreitzer and Stella, 2009, "The therapeutic potential of novel cannabinoid receptors", Pharmacology & Therapeutics 122 (2): 83-96). The human body manufactures a similar class of cannabinoids known as the endocannabinoids which are chemically similar to plant-derived cannabinoids and appear to serve many functions in human physiology (Pertwee et al., 2010, "International Union of Basic and Clinical Pharmacology. LXXIX. Cannabinoid Receptors and Their Ligands: Beyond CB1 and CB2", Pharmacological Reviews 62 (4): 588-631).

Expanding clinical research on the medicinal effects of cannabinoids on human health continue to provide traction to an ever-increasing health and wellness market (Scott et al., 2014, "The Combination of Cannabidiol and Δ9-Tetrahydrocannabinol Enhances the Anticancer Effects of Radiation in an Orthotopic Murine Glioma Model", Molecular Cancer Therapeutics 13 (12): 2955-2967). The past 15 years has seen medical marijuana and hemp gain regulatory favor of equal magnitude. Of course, production of hemp-derived cannabinoids which, by definition, are low in THC is highly desirable among patients and regulatory agencies.

Terpenes serve many functions in the plant and including vital physiological processes. Secondary terpenoids are secondary metabolites which are not involved in primary physiological processes but do serve as the primary source of terpenoid structural diversity. The secondary terpenoids are involved many plant stress response mechanisms (Tholl, 2006, "Terpene synthases and the regulation, diversity and biological roles of terpene metabolism", Current Opinion in Plant Biology 9 (3): 297-304). Hops (*Humulus lupulus*) terpenes such as myrcene and humulene are essential beer ingredients due to the aromatic and flavor compounds they provide. *Cannabis* and *Humulus* share a close evolutionary relationship and synthesize many of the same terpenes (including myrcene and humulene), although normally in different ratios.

*Cannabis* is normally dioecious, where male (staminate) and female (pistillate) flowers develop on separate plants in equal ratios. Plants containing both male and female flowers exist and are referred to as monoecious, or hermaphrodite. Female flowers are characterized by pistils protruding from a calyx. The resinous glandular trichomes of the calyx are the primary site of cannabinoid synthesis. The ovaries are contained within the female calyx and, therefore, the calyx is site of seed development after fertilization by male pollen.

Research has shown that sexual type is heritable and that the sex ratio of progeny derived from pistillate plants pollinated by monoecious types can be skewed from the norm of 50:50 (McPhee, 1925, "The influence of environment on sex in hemp", Journal of Agricultural Research 31 (10) 935-942; Schaffner, 1928, "Further experiments in repeated rejuvenations in hemp and their bearing on the general problem of sex", American Journal of Botany 18:324-330). However, it is known that not all monoecious pollen donors will alter sex ratio and that most often this phenomenon occurs when a pistillate plant transitions to a hermaphroditic form due to environmental factors, such as stress (Clarke, 1981, Marijuana Botany, an Advanced Study: The Propagation and Breeding of Distinctive *Cannabis*, Ronin Publishing). In fact, creating an artificial stress to induce hermaphrodeity in pistillate plants was proposed by Clarke (1981, Marijuana Botany, an Advanced Study: The Propagation and Breeding of Distinctive *Cannabis*, Ronin Publishing) as a method for creating a population skewed in favor of female plants. Such a method is not practical for the production of large quantities of seed (e.g. field-scale) if the environmental factors to induce hermaphrodeity of pistillate plants require tight control. A method of producing a population of plants in which the ratio of females is increased as a result of genetic mechanisms would be desirable since it would remove the necessity to identify and control environmental factors necessary for induction of hermaphrodeity in pistillate plants.

There are numerous steps in the development of any novel, desirable plant germplasm. Plant breeding preferably begins with the analysis and definition of problems and weaknesses of the current germplasm, the establishment of program goals, and the definition of specific breeding objectives. The next step is preferable selection of germplasm that possess the traits to meet the program goals. The goal is to combine in a single variety or hybrid an improved combination of desirable traits from the parental germplasm.

SUMMARY OF THE INVENTION

According to the invention, there is provided novel hemp *Cannabis* cultivars, which produce a significantly skewed ratio of female plants. In some embodiments, the cultivar produces an increased number of female plants when compared to a traditional *Cannabis* cultivar grown in the same environment. In some embodiments, the cultivar produces a ratio of a greater number of female than male plants (greater than 50%). In some embodiment, the cultivar produces from about 60% to about 95% female plants. This invention thus relates to the seeds of the hemp *Cannabis* cultivar of the invention, to plants of the hemp *Cannabis* cultivar of the invention, to plant parts of the hemp *Cannabis* cultivar of the invention, to methods for producing a *Cannabis* cultivar produced by crossing the hemp *Cannabis* cultivar of the invention with another *Cannabis* cultivar, and to methods for producing a *Cannabis* cultivar containing in its genetic material one or more backcross conversion traits or transgenes and to the backcross conversion *Cannabis* plants and plant parts produced by those methods.

This invention also relates to *Cannabis* cultivar and plant parts derived from the hemp *Cannabis* cultivar of the invention, to methods for producing other *Cannabis* cultivar derived from hemp *Cannabis* cultivar of the invention and to the *Cannabis* cultivar and their parts derived by the use of those methods. This invention further relates to *Cannabis* cultivar seeds, plants and plant parts produced by crossing the hemp *Cannabis* cultivar of the invention or a backcross conversion of the cultivar of the invention with another *Cannabis* cultivar.

The invention further relates to products and compositions produced or purified from plants of the invention including the stalks, fibers, pulp, flowers, seeds, hemp and the like. Products produced form the hemp cultivar of the invention can include industrial textiles, building materials, foods, personal hygiene products such as soap, lotions, balms and the like, animal bedding, industrial products such as paints, inks, solvents and lubricants, consumer textiles, animal feed, etc. The invention also relates to use of the *Cannabis* plants, plant parts extracts and the like as a flavoring or aromatic component in malt beverages and the like.

*Cannabis* is normally dioecious with male and female flowers developing on separate plants in equal ratios. Because the female is the seed-bearing plant, female gender skew results in an increase in the total seed harvested per area of land farmed (e.g. grain yield). Female gender skew also increases the yield of female floral biomass, cannabinoids, terpenes, and other valuable compounds synthesized within the female floral tissue. The invention provides methods of increasing the yield of cannabinoids and terpenes from *Cannabis* comprising planting seeds of a *Cannabis* cultivar of the invention that produces greater than 50% female plants, allowing seeds to grow into *Cannabis* plants with female buds, harvesting said *Cannabis* plant, or a plant part thereof, and extracting one or more cannabinoids or one or more terpenes from the harvested *Cannabis* plant, or a plant part thereof. Preferably, the plant part is female chaff, buds, or flowers. The invention further provides methods of increasing total *Cannabis* seed harvested per area of land comprising planting seeds of a *Cannabis* cultivar of the invention that produces greater than 50% female plants, allowing said cultivar to grow and develop seed, and harvesting the seed. The cannabinoid, terpene, and seed yield per area of land are increased relative to *Cannabis* cultivars producing about equal numbers of male and female plants.

The present invention also provides single nucleotide polymorphism (SNP) markers associated with female gender skew. Breeding for *Cannabis* plants with female gender skew can be greatly facilitated by the use of marker-assisted selection. The present invention provides and includes a method for screening and selecting a *Cannabis* plant comprising one or more loci associated with female gender skew.

The present invention provides a method of introgressing an allele into a *Cannabis* plant comprising (a) crossing at least one *Cannabis* plant having female gender skew allele SEQ ID NOs: 3, 4, or 5 with at least one second *Cannabis* plant in order to form a population, (b) genotyping with at least one *Cannabis* plant in the formed population with respect to a *Cannabis* genomic nucleic acid marker, and (c) selecting from the population at least one *Cannabis* plant comprising at least one genotype corresponding to a *Cannabis* plant having female gender skew. In certain embodiments, the selected plants are used for further breeding. In certain embodiments of the methods, the population formed, genotyped, and selected from can be a segregating population. The invention further provides a *Cannabis* plant produced by such methods.

The invention further provides a method of introgressing an allele into a *Cannabis* plant comprising: (a) crossing at least one *Cannabis* plant having female gender skew with at least one *Cannabis* plant having no gender skew in order to form a population; (b) screening the population with at least one nucleic acid marker to determine if one or more *Cannabis* plants from the population contains a female gender skew allele, wherein the female gender skew allele is selected from the group of SEQ ID NOs: 3, 4, and 5. In certain embodiments of this method, the population formed, genotyped, and selected from can be a segregating population. The invention provides a *Cannabis* plant obtained by such methods, the *Cannabis* plant comprising a nucleic acid molecule selected from the group of SEQ ID NOs: 3, 4, or 5.

The invention provides a substantially purified nucleic acid molecule for the detection of loci related to female gender skew comprising a nucleic acid molecule selected from the group of SEQ ID NOs: 3, 4, or 5 and complements thereof. The invention further provides assays for detecting female gender skew loci in a *Cannabis* plant.

Methods of identifying *Cannabis* plants comprising at least one allele associated with female gender skew are also provided. In certain embodiments of these methods of identifying a *Cannabis* plant comprising at least one allele associated with female gender skew in a *Cannabis* plant, the methods comprise: (a) genotyping at least one *Cannabis* plant with at least one *Cannabis* genomic nucleic acid marker selected from the group of SEQ ID NOs: 3, 4, and 5, and (b) selecting at least one *Cannabis* plant comprising an allele of at least one of the nucleic acid markers that is associated with female gender skew. In certain embodiments, the at least one *Cannabis* plant genotyped in step (a) and/or the at least one *Cannabis* plant selected in step (b) is a *Cannabis* plant from a population generated by a cross. In certain embodiments, the selected one or more *Cannabis* plants exhibit female gender skew. In certain embodiments, the progeny of the selected one or more *Cannabis* plants are greater than 50% females. In embodiments where the population is generated by a cross, the cross can be of at least one *Cannabis* plant having female gender skew with at least *Cannabis* plant having no gender skew. In still other embodiments, the methods can further comprise the step (c) of assaying the selected *Cannabis* plant for gender skew. In still other embodiments, the methods can further comprise the step of crossing the *Cannabis* plant selected in step (b) to another *Cannabis* plant. In still other embodiments, the methods can further comprise the step of obtaining seed from the *Cannabis* plant selected in step (b).

Also provided herein are *Cannabis* plants obtained by any of these methods of identifying *Cannabis* plants comprising at least one allele associated with female gender skew. In certain embodiments, *Cannabis* plants obtained by these methods can comprise an allele of at least one nucleic acid molecule selected from the group of SEQ ID NOs: 3, 4, and 5 that is associated with female gender skew, and wherein the *Cannabis* plant exhibit female gender skew. In certain embodiments, *Cannabis* plants obtained by these methods are elite *Cannabis* plants.

Methods of introgressing a female gender skew locus into a *Cannabis* plant are also provided. In certain embodiments, these methods of introgressing a female gender skew locus into a *Cannabis* plant comprise: (a) screening a population with at least one nucleic acid marker to determine if one or more *Cannabis* plants from the population contains a female gender skew locus, and (b) selecting from the population at least one *Cannabis* plant comprising an allele of the marker associated with the female gender skew locus. In certain embodiments of these methods, at least one of the markers is as provided in Table 5. In certain embodiments of these methods, at least one of the markers is located within 5 cM, 2 cM, or 1 cM of the female gender skew locus. In certain embodiments of these methods, at least one of the markers is located within 100 Kb of the female gender skew locus. In other embodiments, at least one of the markers is located within 1 Mb, or 1 Kb of the female gender skew locus.

In certain embodiments of these methods, the population is a segregating population. In certain embodiments of these methods, at least one of the markers exhibits a LOD score of greater than 2.0 with the female gender skew locus. In other embodiments, at least one of the markers exhibits a LOD score of greater than 3.0 or greater than 4.0 with the female gender skew locus. In certain embodiments of these methods, at least one of the markers is selected from the group of SEQ ID NOs: 3, 4, and 5.

Also provided herein are *Cannabis* plants obtained by any of these methods of introgressing a female gender skew locus into a *Cannabis* plant. In certain embodiments, a *Cannabis* plant obtained by these methods can comprise an allele of at least one of nucleic acid marker selected from the group of SEQ ID NOs: 3, 4, and 5 that is associated with female gender skew. In certain embodiments, a *Cannabis* plant obtained by these methods can exhibit female gender skew. In certain embodiments, the progeny of a *Cannabis* plant obtained by these methods are greater than 50% females.

Also provided are isolated nucleic acid molecules for detecting a molecular marker representing a polymorphism in *Cannabis* DNA, wherein the nucleic acid molecule comprises at least 15 nucleotides that include or are adjacent to the polymorphism, wherein the nucleic acid molecule is at least 70%, 80%, 90%, 95%, 98%, or 99% identical to a sequence of the same number of consecutive nucleotides in either strand of DNA that include or are adjacent to the polymorphism, and wherein the molecular marker is selected from the group of SEQ ID NOs: 3, 4, and 5. In some embodiments, the polymorphism is an 'A' at position 51, a 'T' at position 56, or an 'A' at position 58 as set forth in SEQ ID NOs: 3, 4, and 5. In some embodiments, isolated nucleic acid molecules comprising SEQ ID NO: 3, 4, or 5, or a nucleotide sequence having at least 70%, 80%, 90%, 95%, 98%, or 99% sequence identity to SEQ ID NO: 3, 4, or 5 that include an 'A' at position 51, a 'T' at position 56, and/or an 'A' at position 58 are provided. In at least some embodiments the nucleic acid includes one or more base changes so that the sequence is not the naturally occurring sequence. In certain embodiments, the nucleic acids can further comprise a detectable label or provide for incorporation of a detectable label. In certain embodiments, the nucleic acid molecule hybridizes to at least one allele of the molecular marker under stringent hybridization conditions.

DETAILED DESCRIPTION OF THE INVENTION

Definitions

In the description and tables which follow, a number of terms are used. In order to provide a clear and consistent understanding of the present invention, the following definitions are provided:

The invention provides *Cannabis* plants. As used herein, the term "plant" refers to plants in the genus of *Cannabis* and plants derived thereof. Such as *Cannabis* plants produced via asexual reproduction and via seed production.

The invention provides plant parts. As used herein, the term "plant part" refers to any part of a plant including but not limited to the embryo, shoot, root, stem, seed, stipule, leaf, petal, flower bud, flower, ovule, bract, trichome, branch, petiole, internode, bark, pubescence, tiller, rhizome, frond, blade, ovule, pollen, stamen, and the like. The two main parts of plants grown in some sort of media, such as soil or vermiculite, are often referred to as the "above-ground" part, also often referred to as the "shoots", and the "below-ground" part, also often referred to as the "roots". Plant part may also include certain extracts such as kief or hash which includes *Cannabis* trichomes or glands.

The term "a" or "an" refers to one or more of that entity; for example, "a gene" refers to one or more genes or at least one gene. As such, the terms "a" (or "an"), "one or more" and "at least one" are used interchangeably herein. In addition, reference to "an element" by the indefinite article "a" or "an" does not exclude the possibility that more than one of the elements is present, unless the context clearly requires that there is one and only one of the elements.

As used herein, a "landrace" refers to a local variety of a domesticated plant species which has developed largely by natural processes, by adaptation to the natural and cultural environment in which it lives. The development of a landrace may also involve some selection by humans but it differs from a formal breed which has been selectively bred deliberately to conform to a particular formal, purebred standard of traits.

The invention provides plant cultivars. As used herein, the term "cultivar" means a group of similar plants that by structural features and performance (i.e., morphological and physiological characteristics) can be identified from other varieties within the same species. Furthermore, the term "cultivar" variously refers to a variety, strain or race of plant that has been produced by horticultural or agronomic techniques and is not normally found in wild populations. The terms cultivar, variety, strain and race are often used interchangeably by plant breeders, agronomists and farmers.

The term "variety" as used herein has identical meaning to the corresponding definition in the International Convention for the Protection of New Varieties of Plants (UPOV treaty), of Dec. 2, 1961, as Revised at Geneva on Nov. 10, 1972, on Oct. 23, 1978, and on Mar. 19, 1991. Thus, "variety" means a plant grouping within a single botanical taxon of the lowest known rank, which grouping, irrespective of whether the conditions for the grant of a breeder's right are fully met, can be i) defined by the expression of the characteristics resulting from a given genotype or combination of genotypes, ii) distinguished from any other plant grouping by the expression of at least one of the said characteristics and iii) considered as a unit with regard to its suitability for being propagated unchanged.

"Elite line" means any line that has resulted from breeding and selection for superior agronomic performance. An "elite population" is an assortment of elite individuals or lines that can be used to represent the state of the art in terms of agronomically superior genotypes of a given crop species. Similarly, an "elite germplasm" or elite strain of germplasm is an agronomically superior germplasm.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leaves, stems, pollen, or cells that can be cultured into a whole plant.

As used herein, the term "inbreeding" refers to the production of offspring via the mating between relatives. The plants resulting from the inbreeding process are referred to herein as "inbred plants" or "inbreds."

The term LOQ as used herein refers to the limit of quantitation for Gas Chromatography (GC) and High Performance Liquid Chromatography measurements.

The term secondary metabolites as used herein refers to organic compounds that are not directly involved in the normal growth, development, or reproduction of an organism. In other words, loss of secondary metabolites does not result in immediate death of said organism.

The term single allele converted plant as used herein refers to those plants which are developed by a plant breeding technique called backcrossing wherein essentially all of the desired morphological and physiological characteristics of an inbred are recovered in addition to the single allele transferred into the inbred via the backcrossing technique.

"Allele" refers to an alternative nucleic acid sequence at a particular locus; the length of an allele can be as small as 1 nucleotide base, but is typically larger. For example, a first allele can occur on one chromosome, while a second allele occurs on a second homologous chromosome, e.g., as occurs for different chromosomes of a heterozygous individual, or between different homozygous or heterozygous individuals in a population. A favorable allele is the allele at a particular locus that confers, or contributes to, an agronomically desirable phenotype, or alternatively, is an allele that allows the identification of plants that can be removed from a breeding program or planting. A favorable allele of a marker is a marker allele that segregates with the favorable phenotype, or alternatively, segregates with an unfavorable plant phenotype, therefore providing the benefit of identifying plants having the unfavorable phenotype. A favorable allelic form of a chromosome interval is a chromosome interval that includes a nucleotide sequence that contributes to superior agronomic performance at one or more genetic loci physically located on the chromosome interval. "Allele frequency" refers to the frequency (proportion or percentage) at which an allele is present at a locus within an individual, within a line, or within a population of lines. For example, for an allele "A," diploid individuals of genotype "AA," "Aa," or "aa" have allele frequencies of 1.0, 0.5, or 0.0, respectively. One can estimate the allele frequency within a line by averaging the allele frequencies of a sample of individuals from that line. Similarly, one can calculate the allele frequency within a population of lines by averaging the allele frequencies of lines that make up the population. For a population with a finite number of individuals or lines, an allele frequency can be expressed as a count of individuals or lines (or any other specified grouping) containing the allele. An allele positively correlates with a trait when it is linked to it and when presence of the allele is an indicator that the desired trait or trait form will occur in a plant comprising the allele. An allele negatively correlates with a trait when it is linked to it and when presence of the allele is an indicator that a desired trait or trait form will not occur in a plant comprising the allele.

"Locus" a chromosome region where a polymorphic nucleic acid, trait determinant, gene or marker is located. The loci of this invention comprise one or more polymorphisms in a population; i.e., alternative alleles are present in some individuals. A "gene locus" is a specific chromosome location in the genome of a species where a specific gene can be found.

"Linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Linked loci co-segregate more than 50% of the time, e.g., from about 51% to about 100% of the time. The tern "physically linked" is sometimes used to indicate that two loci, e.g., two marker loci, are physically present on the same chromosome. Advantageously, the two linked loci are located in close proximity such that recombination between homologous chromosome pairs does not occur between the two loci during meiosis with high frequency, e.g., such that linked loci cosegregate at least about 90% of the time, e.g., 91%, 92%, 93%, 94%, 95%, 96%, 97%, 98%, 99%, 99.5%, 99.75%, or more of the time.

"Marker Assay" means a method for detecting a polymorphism at a particular locus using a particular method, e.g. measurement of at least one phenotype (such as seed color, flower color, or other visually detectable trait), restriction fragment length polymorphism (RFLP), single base extension, electrophoresis, sequence alignment, allelic specific oligonucleotide hybridization (ASO), random amplified polymorphic DNA (RAPD), microarray-based technologies, and nucleic acid sequencing technologies, etc. "Marker Assisted Selection" (MAS) is a process by which phenotypes are selected based on marker genotypes.

The invention provides samples. As used herein, the term "sample" includes a sample from a plant, a plant part, a plant cell, or from a transmission vector, or a soil, water or air sample.

The invention provides progeny. As used herein, the term "progeny" refers to any plant resulting from a vegetative or sexual reproduction from one or more parent plants or descendants thereof. For instance, a progeny plant may be obtained by cloning or selfing of a parent plant or by crossing two parent plants and include selfings as well as the F1 or F2 or still further generations. An F1 is a first-generation progeny produced from parents at least one of which is used for the first time as donor of a trait, while offspring of second generation (F2) or subsequent generations (F3, F4, etc.) are specimens produced from selfings of F1's F2's etc. An F1 may thus be (and usually is) a hybrid resulting from a cross between two true breeding parents (true-breeding is homozygous for a trait), while an F2 may be (and usually is) an progeny resulting from self-pollination of said F1 hybrids.

The invention provides methods for crossing a first plant with a second plant. As used herein, the term "cross", "crossing", "cross pollination" or "cross-breeding" refer to the process by which the pollen of one flower on one plant is applied (artificially or naturally) to the ovule (stigma) of a flower on another plant. Backcrossing is a process in which a breeder repeatedly crosses hybrid progeny, for example a first generation hybrid (F1), back to one of the parents of the hybrid progeny. Backcrossing can be used to introduce one or more single locus conversions from one genetic background into another.

The term backcrossing is a process in which a breeder crosses progeny back to one of the parents one or more times, for example, a first generation hybrid $F_1$ with one of the parental genotype of the $F_1$ hybrid.

The invention provides donor plants and recipient plants. As used herein, "donor plants" refer to the parents of a variety which contains the gene or trait of interest which is desired to be introduced into a second variety (e.g., "recipient plants").

In some embodiments, the present invention provides methods for obtaining plant genotypes comprising recombinant genes. As used herein, the term "genotype" refers to the genetic makeup of an individual cell, cell culture, tissue, organism (e.g., a plant), or group of organisms. A "haplotype" is the genotype of an individual at a plurality of genetic loci. Typically, the genetic loci described by a haplotype are physically and genetically linked, i.e., on the same chromosome interval. The terms "phenotype," or "phenotypic trait" or "trait" refers to one or more trait of an organism.

The phenotype can be observable to the naked eye, or by any other means of evaluation known in the art, e.g., microscopy, biochemical analysis, genomic analysis, an assay for a particular disease tolerance, etc. In some cases, a phenotype is directly controlled by a single gene or genetic locus, i.e., a "single gene trait." In other cases, a phenotype is the result of several genes. "Phenotype" means the detectable characteristics of a cell or organism which can be influenced by genotype.

"Molecular phenotype" is a phenotype detectable at the level of a population of one or more molecules. Such molecules can be nucleic acids, proteins, or metabolites. A molecular phenotype could be an expression profile for one or more gene products, e.g., at a specific stage of plant development, in response to an environmental condition or stress, etc.

A "population of plants" or "plant population" means a set comprising any number, including one, of individuals, objects, or data from which samples are taken for evaluation, e.g. estimating QTL effects. Most commonly, the terms relate to a breeding population of plants from which members are selected and crossed to produce progeny in a breeding program. A population of plants can include the progeny of a single breeding cross or a plurality of breeding crosses, and can be either actual plants or plant derived material, or in silico representations of the plants. The population members need not be identical to the population members selected for use in subsequent cycles of analyses or those ultimately selected to obtain final progeny plants. Often, a plant population is derived from a single biparental cross, but may also derive from two or more crosses between the same or different parents. Although a population of plants may comprise any number of individuals, those of skill in the art will recognize that plant breeders commonly use population sizes ranging from one or two hundred individuals to several thousand, and that the highest performing 5-20% of a population is what is commonly selected to be used in subsequent crosses in order to improve the performance of subsequent generations of the population.

In some embodiments, the present invention provides homozygotes. As used herein, the term "homozygote" refers to an individual cell or plant having the same alleles at one or more loci.

In some embodiments, the present invention provides homozygous plants. As used herein, the term "homozygous" refers to the presence of identical alleles at one or more loci in homologous chromosomal segments.

In some embodiments, the present invention provides hemizygotes. As used herein, the term "hemizygotes" or "hemizygous" refers to a cell, tissue, organism or plant in which a gene is present only once in a genotype, as a gene in a haploid cell or organism, a sex-linked gene in the heterogametic sex, or a gene in a segment of chromosome in a diploid cell or organism where its partner segment has been deleted.

In some embodiments, the present invention provides heterozygotes. As used herein, the terms "heterozygote" and "heterozygous" refer to a diploid or polyploid individual cell or plant having different alleles (forms of a given gene) present at least at one locus. In some embodiments, the cell or organism is heterozygous for the gene of interest which is under control of the synthetic regulatory element.

The invention provides methods for obtaining plant lines comprising recombinant genes. As used herein, the term "line" is used broadly to include, but is not limited to, a group of plants vegetatively propagated from a single parent plant, via tissue culture techniques or a group of inbred plants which are genetically very similar due to descent from a common parent(s). A plant is said to "belong" to a particular line if it (a) is a primary transformant (T0) plant regenerated from material of that line; (b) has a pedigree comprised of a T0 plant of that line; or (c) is genetically very similar due to common ancestry (e.g., via inbreeding or selfing). In this context, the term "pedigree" denotes the lineage of a plant, e.g. in terms of the sexual crosses affected such that a gene or a combination of genes, in heterozygous (hemizygous) or homozygous condition, imparts a desired trait to the plant.

The invention provides open-pollinated populations. As used herein, the terms "open-pollinated population" or "open-pollinated variety" refer to plants normally capable of at least some cross-fertilization, selected to a standard, that may show variation but that also have one or more genotypic or phenotypic characteristics by which the population or the variety can be differentiated from others. A hybrid, which has no barriers to cross-pollination, is an open-pollinated population or an open-pollinated variety.

The invention provides self-pollination populations. As used herein, the term "self-crossing", "self-pollinated" or "self-pollination" means the pollen of one flower on one plant is applied (artificially or naturally) to the ovule (stigma) of the same or a different flower on the same plant.

The invention provides ovules and pollens of plants. As used herein when discussing plants, the term "ovule" refers to the female gametophyte, whereas the term "pollen" means the male gametophyte.

The invention provides plant tissue. As used herein, the term "plant tissue" refers to any part of a plant. Examples of plant organs include, but are not limited to the leaf, stem, root, tuber, seed, branch, pubescence, nodule, leaf axil, flower, pollen, stamen, pistil, petal, peduncle, stalk, stigma, style, bract, fruit, trunk, carpel, sepal, anther, ovule, pedicel, needle, cone, rhizome, stolon, shoot, pericarp, endosperm, placenta, berry, stamen, and leaf sheath.

The invention provides methods for obtaining plants comprising recombinant genes through transformation. As used herein, the term "transformation" refers to the transfer of nucleic acid (i.e., a nucleotide polymer) into a cell. As used herein, the term "genetic transformation" refers to the transfer and incorporation of DNA, especially recombinant DNA, into a cell.

The invention provides transformants comprising recombinant genes. As used herein, the term "transformant" refers to a cell, tissue or organism that has undergone transformation. The original transformant is designated as "T0" or "$T_0$." Selfing the T0 produces a first transformed generation designated as "T1" or "$T_1$."

In some embodiments, the present invention provides organisms with recombinant genes. As used herein, an "organism" refers any life form that has genetic material comprising nucleic acids including, but not limited to, prokaryotes, eukaryotes, and viruses. Organisms of the present invention include, for example, plants, animals, fungi, bacteria, and viruses, and cells and parts thereof.

As used herein, the term "female" refers to *Cannabis* plants carrying only pistillate flowers and devoid of pollen. The term "bud" refers to *Cannabis* female floral tissue collected prior to seed harvest from the apical meristems. The term "chaff" refers to *Cannabis* bud tissue collected after threshing and separation of physiologically mature seed from the bud. The term "male" refers to *Cannabis* plants carrying only staminate flowers producing pollen.

"Recombinant" in reference to a nucleic acid or polypeptide indicates that the material (e.g., a recombinant nucleic acid, gene, polynucleotide, polypeptide, etc.) has been altered by human intervention. The term recombinant can also refer to an organism that harbors recombinant material, e.g., a plant that comprises a recombinant nucleic acid is considered a recombinant plant.

"Exogenous nucleic acid" is a nucleic acid that is not native to a specified system (e.g., a germplasm, plant, variety, etc.), with respect to sequence, genomic position, or both. As used herein, the terms "exogenous" or "heterologous" as applied to polynucleotides or polypeptides typically refers to molecules that have been artificially supplied to a biological system (e.g., a plant cell, a plant gene, a particular plant species or variety or a plant chromosome under study) and are not native to that particular biological system. The terms can indicate that the relevant material originated from a source other than a naturally occurring source, or can refer to molecules having a non-natural configuration, genetic location or arrangement of parts. In contrast, for example, a "native" or "endogenous" gene is a gene that does not contain nucleic acid elements encoded by sources other than the chromosome or other genetic element on which it is normally found in nature. An endogenous gene, transcript or polypeptide is encoded by its natural chromosomal locus, and not artificially supplied to the cell.

"Genetic element" or "gene" refers to a heritable sequence of DNA, i.e., a genomic sequence, with functional significance. The term "gene" can also be used to refer to, e.g., a cDNA and/or an mRNA encoded by a genomic sequence, as well as to that genomic sequence.

"Polymorphism" means the presence of one or more variations in a population. A polymorphism may manifest as a variation in the nucleotide sequence of a nucleic acid or as a variation in the amino acid sequence of a protein. Polymorphisms include the presence of one or more variations of a nucleic acid sequence or nucleic acid feature at one or more loci in a population of one or more individuals. The variation may comprise but is not limited to one or more nucleotide base changes, the insertion of one or more nucleotides or the deletion of one or more nucleotides. A polymorphism may arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found or may exist at low frequency within a population, the former having greater utility in general plant breeding and the latter may be associated with rare but important phenotypic variation. Useful polymorphisms may include single nucleotide polymorphisms (SNPs), insertions or deletions in DNA sequence (Indels), simple sequence repeats of DNA sequence (SSRs), a restriction fragment length polymorphism, and a tag SNP. A genetic marker, a gene, a DNA-derived sequence, a RNA-derived sequence, a promoter, a 5' untranslated region of a gene, a 3' untranslated region of a gene, microRNA, siRNA, a tolerance locus, a satellite marker, a transgene, mRNA, ds mRNA, a transcriptional profile, and a methylation pattern may also comprise polymorphisms. In addition, the presence, absence, or variation in copy number of the preceding may comprise polymorphisms.

"Operably linked" refers to the association of two or more nucleic acid elements in a recombinant DNA construct, e.g. as when a promoter is operably linked with DNA that is transcribed to RNA whether for expressing or suppressing a protein. Recombinant DNA constructs can be designed to express a protein which can be an endogenous protein, an exogenous homologue of an endogenous protein or an exogenous protein with no native homologue. Alternatively, recombinant DNA constructs can be designed to suppress the level of an endogenous protein, e.g. by suppression of the native gene. Such gene suppression can be effectively employed through a native RNA interference (RNAi) mechanism in which recombinant DNA comprises both sense and anti-sense oriented DNA matched to the gene targeted for suppression where the recombinant DNA is transcribed into RNA that can form a double-strand to initiate an RNAi mechanism. Gene suppression can also be effected by recombinant DNA that comprises anti-sense oriented DNA matched to the gene targeted for suppression. Gene suppression can also be effected by recombinant DNA that comprises DNA that is transcribed to a microRNA matched to the gene targeted for suppression.

"Adjacent", when used to describe a nucleic acid molecule that hybridizes to DNA containing a polymorphism, refers to a nucleic acid that hybridizes to DNA sequences that directly abut the polymorphic nucleotide base position. For example, a nucleic acid molecule that can be used in a single base extension assay is "adjacent" to the polymorphism.

As used herein, "consensus sequence" refers to a constructed DNA sequence which identifies SNP and Indel polymorphisms in alleles at a locus. Consensus sequence can be based on either strand of DNA at the locus and states the nucleotide base of either one of each SNP in the locus and the nucleotide bases of all Indels in the locus. Thus, although a consensus sequence may not be a copy of an actual DNA sequence, a consensus sequence is useful for precisely designing primers and probes for actual polymorphisms in the locus.

"Transgenic plant" refers to a plant that comprises within its cells a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to refer to any cell, cell line, callus, tissue, plant part or plant, the genotype of which has been altered by the presence of heterologous nucleic acid including those transgenic organisms or cells initially so altered, as well as those created by crosses or asexual propagation from the initial transgenic organism or cell. The term "transgenic" as used herein does not encompass the alteration of the genome (chromosomal or extrachromosomal) by conventional plant breeding methods (e.g., crosses) or by naturally occurring events such as random cross-fertilization, non-recombinant viral infection, non-recombinant bacterial transformation, non-recombinant transposition, or spontaneous mutation.

"Vector" is a polynucleotide or other molecule that transfers nucleic acids between cells. Vectors are often derived from plasmids, bacteriophages, or viruses and optionally comprise parts which mediate vector maintenance and enable its intended use. A "cloning vector" or "shuttle vector" or "subcloning vector" contains operably linked parts that facilitate subcloning steps (e.g., a multiple cloning site containing multiple restriction endonuclease sites). The term "expression vector" as used herein refers to a vector comprising operably linked polynucleotide sequences that facilitate expression of a coding sequence in a particular host organism (e.g., a bacterial expression vector or a plant expression vector).

"Gender skew" and "sex ratio" refer to the proportion of male and female progeny produced by a *Cannabis* plant. A *Cannabis* plant that produces a greater number of female than male plants (greater than 50% females) is said to exhibit "female gender skew". A *Cannabis* plant that produces approximately equal numbers of female and male plants (about 50% males and about 50% females) is said to have "no gender skew". In some embodiments, the *Cannabis* plants having female gender skew produce greater than 50% female plants, greater than 60% females, greater than 70% females, greater than 80% females, greater than 90% females, greater than 95% or more and percentages in-between. In some embodiments, the *Cannabis* plants having female gender skew produce from about 51% to about 100% females, preferably from about 60% to about 95% females.

"Female gender skew allele" refers to the nucleic acid sequence associated female gender skew in *Cannabis* plants at a particular locus.

"Female gender skew locus" refers to a locus associated with female gender skew in *Cannabis* plants.

*Cannabis Cannabis* has long been used for drug and industrial purposes including fiber, seed and seed oils, and for medicinal purposes. Industrial hemp fiber products are made from *Cannabis* plants selected to produce an abundance of stalk tissue from which fiber is created.

*Cannabis* plants produce a unique family of terpenophenolic compounds called cannabinoids. Cannabinoids, terpenoids, and other compounds are secreted by glandular trichomes that occur most abundantly on the floral calyxes and bracts of female plants. As a drug it usually comes in the form of dried flower buds (marijuana), resin (hashish), or various extracts collectively known as hashish oil. There are at least 483 identifiable chemical constituents known to exist in the *Cannabis* plant (Rudolf Brenneisen, 2007, Chemistry and Analysis of Phytocannabinoids (cannabinoids produced by *Cannabis*) and other *Cannabis* Constituents, In Marijuana and the Cannabinoids, ElSohly, ed.; incorporated herein by reference) and at least 85 different cannabinoids have been isolated from the plant (El-Alfy, Abir T, et al., 2010, "Antidepressant-like effect of delta-9-tetrahydrocannabinol and other cannabinoids isolated from *Cannabis sativa* L", Pharmacology Biochemistry and Behavior 95 (4): 434-42; incorporated herein by reference). The two cannabinoids usually produced in greatest abundance are cannabidiol (CBD) and/or Δ-9-tetrahydrocannabinol (THC). THC is psychoactive while CBD is not. See, ElSohly, ed. (Marijuana and the Cannabinoids, Humana Press Inc., 321 papers, 2007), which is incorporated herein by reference in its entirety, for a detailed description and literature review on the cannabinoids found in marijuana.

Cannabinoids are the most studied group of secondary metabolites in *Cannabis*. Most exist in two forms, as acids and in neutral (decarboxylated) forms. The acid form is designated by an "A" at the end of its acronym (i.e. THCA). The phytocannabinoids are synthesized in the plant as acid forms, and while some decarboxylation does occur in the plant, it increases significantly post-harvest and the kinetics increase at high temperatures. (Sanchez and Verpoorte 2008). The biologically active forms for human consumption are the neutral forms. Decarboxylation is usually achieved by thorough drying of the plant material followed by heating it, often by either combustion, vaporization, or heating or baking in an oven. Unless otherwise noted, references to cannabinoids in a plant include both the acidic and decarboxylated versions (e.g., CBD and CBDA).

The cannabinoids in *Cannabis* plants include, but are not limited to, Δ 9 Tetrahydrocannabinol (Δ9-THC), Δ. 8-Tetrahydrocannabinol (Δ8-THC), Cannabichromene (CBC), Cannabicyclol (CBL), Cannabidiol (CBD), Cannabielsoin (CBE), Cannabigerol (CBG), Cannabinidiol (CBND), Cannabinol (CBN), Cannabitriol (CBT), and their propyl homologs, including, but are not limited to cannabidivarin (CBDV), Δ.9-Tetrahydrocannabivarin (THCV), cannabichromevarin (CBCV), and cannabigerovarin (CBGV). See Holley et al. (Constituents of *Cannabis sativa* L. XI Cannabidiol and cannabichromene in samples of known geographical origin, J. Pharm. Sci. 64:892-894, 1975) and De Zeeuw et al. (Cannabinoids with a propyl side chain in *Cannabis*, Occurrence and chromatographic behavior, Science 175:778-779), each of which is herein incorporated by reference in its entirety for all purposes. Non-THC cannabinoids can be collectively referred to as "CBs", wherein CBs can be one of THCV, CBDV, CBGV, CBCV, CBD, CBC, CBE, CBG, CBN, CBND, and CBT cannabinoids.

Female Gender Skew

*Cannabis* is normally dioecious with male and female flowers developing on separate plants in equal ratios. Because the female is the seed-bearing plant, any increase in the frequency of female plants ("female gender skew") in a population should result in an increase in the total seed harvested per area of land farmed (e.g grain yield). It would also increase the yield of female floral biomass and, concordantly, the yield of cannabinoids, terpenoids and other valuable compounds synthesized within the female floral tissue. The increase in the frequency of female plants also provides a population of primarily male sterile plants for the production of hybrids. The *Cannabis* cultivars of the invention can be used in methods of production in which skewed $F_1$ seed is used as a female to cross with a second gender-skew male. The skewed $F_1$ is akin to a cytoplasmic male sterile line which allows the seed to be produced on a much larger scale.

The present invention identifies previously-unknown genetic loci which confer female gender skew, and provides novel molecular markers linked to female gender skew in *Cannabis* plants. The invention further provides methods for introgression of genetic loci conferring female gender skew into plant varieties previously lacking such loci. The genetic loci, markers, and methods provided by the invention therefore represent a significant advance in the art, enabling production of new varieties with an increase in the frequency of female plants.

In some embodiments, the invention therefore provides quantitative trait loci (QTL) that demonstrate significant co-segregation with female gender skew. The QTL of the invention can be tracked during plant breeding or introgressed into a desired genetic background in order to provide novel plants exhibiting female gender skew and one or more other beneficial traits. In particular embodiments, the invention identifies for the first time a locus on chromosome 4 of the *Cannabis* genome, which is associated with female gender skew. In some embodiments, the *Cannabis* cultivars of the invention comprise at least one polymorphism selected from an 'A' at position 43581285, a 'T' at position 43581290, and an 'A' at position 43581292 with reference to the position numbering of chromosome 4 (CM011608.1).

In other embodiments, the invention provides molecular markers linked to the QTL of the invention and methods of using the markers for detection of and selection for female gender skew. Embodiments of the invention therefore include specific markers, chromosome intervals comprising the markers, and methods of detecting markers genetically linked to the locus on chromosome 4 to identify plant lines with favorable gender skew. In certain embodiments, the invention further provides markers closely genetically linked to SEQ ID NOs: 3, 4 or 5, and chromosome intervals whose borders include such markers. Also provided herein are markers that are useful for detecting the presence or absence of female gender skew alleles within the QTL of the invention that can be used in marker assisted selection (MAS) breeding programs to produce plants with female gender skew.

The invention further provides methods of using the markers identified herein to introgress loci associated with female gender skew into plants. Thus, one skilled in the art can use the invention to create novel *Cannabis* plants with female gender skew by crossing a donor line comprising a QTL associated with female gender skew into any desired recipient line, with or without MAS. Resulting progeny can be selected to be genetically similar to the recipient line except for the female gender skew QTL.

Quantitative Trait Loci

The term "chromosome interval" designates a contiguous linear span of genomic DNA that resides on a single chromosome. A chromosome interval may comprise a QTL linked with a genetic trait and the QTL may comprise a single gene or multiple genes associated with the genetic trait. The boundaries of a chromosome interval comprising a QTL are drawn such that a marker that lies within the chromosome interval can be used as a marker for the genetic trait, as well as markers genetically linked thereto. Each interval comprising a QTL comprises at least one gene conferring a given trait, however knowledge of how many genes are in a particular interval is not necessary to make or practice the invention, as such an interval will segregate at meiosis as a linkage block. In accordance with the invention, a chromosomal interval comprising a QTL may therefore be readily introgressed and tracked in a given genetic background using the methods and compositions provided herein.

Identification of chromosomal intervals and QTL is therefore beneficial for detecting and tracking a genetic trait, such as female gender skew, in plant populations. In some embodiments, this is accomplished by identification of markers linked to a particular QTL. The principles of QTL analysis and statistical methods for calculating linkage between markers and useful QTL include penalized regression analysis, ridge regression, single point marker analysis, complex pedigree analysis, Bayesian MCMC, identity-by-descent analysis, interval mapping, composite interval mapping (CIM), and Haseman-Elston regression. QTL analyses may be performed with the help of a computer and specialized software available from a variety of public and commercial sources known to those of skill in the art.

In some embodiments, the invention provides a chromosomal interval comprising a QTL associated with female gender skew. The invention also provides multiple markers associated with female gender skew, for example the markers having the sequence of SEQ ID NOs: 3, 4, and 5. The invention therefore provides plants comprising a nucleic acid molecule selected from the group consisting of SEQ ID NOs: 3, 4, and 5, fragments thereof, or complements thereof. The present invention further provides a plant comprising alleles of the chromosome interval linked to female gender skew or fragments and complements thereof as well as any plant comprising any combination of one or more female gender skew loci selected from the group consisting of SEQ ID NOs: 3, 4, and 5. Plants provided by the invention may be homozygous or heterozygous for such alleles.

Thus, one skilled in the art can use the invention to create novel *Cannabis* plants with female gender skew by associating gender skew phenotypes with genotypes at previously unknown gender skew loci in the *Cannabis* genome. Disclosed herein are chromosome intervals that comprise alleles responsible for phenotypic differences between *Cannabis* lines with favorable or unfavorable gender skew. The chromosome intervals of the invention are characterized in specific embodiments by genomic regions including the markers SEQ ID NOs: 3, 4, and 5, which comprise markers closely linked to (within 20 cM of) the gender skew locus on chromosome 4.

Examples of markers useful for this purpose comprise the SNP markers listed in Table 5, or any marker linked thereto, including a marker that maps within or is genetically linked to the chromosome intervals described herein, including the termini of the intervals. Such markers can be assayed simultaneously or sequentially in a single sample or population of samples.

Accordingly, the compositions and methods of the present invention can be utilized to guide MAS or breeding *Cannabis* varieties with a desired complement (set) of allelic forms of chromosome intervals associated with superior agronomic performance (female gender skew, along with any other available markers for yield, disease tolerance, etc.). Any of the disclosed marker alleles can be introduced into a *Cannabis* line via introgression, by traditional breeding (or introduced via transformation, or both) to yield a *Cannabis* plant with superior agronomic performance. The number of alleles associated with female gender skew that can be introduced or be present in a *Cannabis* plant of the present invention ranges from 1 to the number of alleles disclosed herein, each integer of which is incorporated herein as if explicitly recited.

MAS using additional markers flanking either side of the DNA locus provide further efficiency because an unlikely double recombination event would be needed to simultaneously break linkage between the locus and both markers. Moreover, using markers tightly flanking a locus, one skilled in the art of MAS can reduce linkage drag by more accurately selecting individuals that have less of the potentially deleterious donor parent DNA. Any marker linked to or among the chromosome intervals described herein can thus find use within the scope of this invention.

Similarly, by identifying plants lacking a desired marker locus, plants having unfavorable gender skew (male gender skew or no gender skew) can be identified and eliminated from subsequent crosses. These marker loci can be introgressed into any desired genomic background, germplasm, plant, line, variety, etc., as part of an overall MAS breeding program designed to enhance gender skew. The invention also provides chromosome QTL intervals that can be used in MAS to select plants that demonstrate female gender skew. The present invention also extends to a method of making a progeny Cannabis plant and the resulting progeny Cannabis plants. The method comprises, in an embodiment, crossing a first parent Cannabis plant with a second Cannabis plant and growing the female Cannabis plant parent under plant growth conditions to yield Cannabis plant progeny. Methods of crossing and growing Cannabis plants are well within the ability of those of ordinary skill in the art. Such Cannabis plant progeny can be assayed for alleles associated with female gender skew as disclosed herein and, thereby, the desired progeny selected. Such progeny plants or seed thereof can be sold commercially for Cannabis production, used for food or feed, processed to obtain a desired constituent of the Cannabis, or further utilized in subsequent rounds of breeding. At least one of the first or second Cannabis plants may be a Cannabis plant of the present invention in that it comprises at least one of the allelic forms of the markers of the present invention, such that the progeny are capable of inheriting the allele.

Often, a method of the present invention may be applied to at least one related Cannabis plant such as from a progenitor or descendant line in the subject Cannabis plants' pedigree such that inheritance of the desired allele can be traced. The number of generations separating the Cannabis plants being subjected to the methods of the present invention may be, in specific embodiments, from 1 to 20 or more, commonly 1 to 10, and including 1, 2, 3, 4, 5, 6, 7, 8, 9, 10 or more generations of separation, and often a direct descendant or parent of the Cannabis plant will be subject to the method (i.e., one generation of separation).

Thus, the invention permits one skilled in the art to detect the presence or absence of gender skew genotypes in the genomes of Cannabis plants as part of a MAS program. In one embodiment, a breeder ascertains the genotype at one or more markers for a parent having favorable gender skew, which contains a female gender skew allele, and the genotype at one or more markers for a parent with unfavorable gender skew, which lacks the female gender skew allele. For example, the markers of the present invention can be used in MAS in crosses involving elite and exotic Cannabis lines by subjecting the segregating progeny to MAS to maintain gender skew alleles. A breeder can then reliably track the inheritance of the gender skew alleles through subsequent populations derived from crosses between the two parents by genotyping offspring with the markers used on the parents and comparing the genotypes at those markers with those of the parents. Depending on how tightly linked the marker alleles are with the trait, progeny that share genotypes with the parent having favorable gender skew alleles can be reliably predicted to express the desirable phenotype and progeny that share genotypes with the parent having unfavorable gender skew alleles can be reliably predicted to express the undesirable phenotype.

By providing the positions in the Cannabis genome of gender skew chromosome intervals and the associated markers within those intervals, the invention also allows one skilled in the art to identify and use other markers within the intervals disclosed herein or linked to the intervals disclosed herein. Having identified such regions, these markers can be readily identified from public linkage maps.

Closely linked markers flanking the locus of interest that have alleles in linkage disequilibrium with a gender skew allele at that locus may be effectively used to select for progeny plants with desirable gender skew. Thus, the markers described herein, such as those listed in Table 5, as well as other markers genetically linked to the same chromosome interval, may be used to select for Cannabis plants with female gender skew. Often, a set of these markers will be used, (e.g., 2 or more, 3 or more, 4 or more, 5 or more) in the flanking regions of the locus. Optionally, as described above, a marker flanking or within the actual locus may also be used. The parents and their progeny may be screened for these sets of markers, and the markers that are polymorphic between the two parents used for selection. In an introgression program, this allows for selection of the gene or locus genotype at the more proximal polymorphic markers and selection for the recurrent parent genotype at the more distal polymorphic markers.

The choice of markers actually used to practice the invention is not limited and can be any marker that is genetically linked to the intervals as described herein, which includes markers mapping within the intervals. In certain embodiments, the invention further provides markers closely genetically linked to, or within approximately 0.5 cM of, the markers provided herein and chromosome intervals whose borders fall between or include such markers, and including markers within approximately 0.4 cM, 0.3 cM, 0.2 cM, and about 0.1 cM of the markers provided herein. Furthermore, since there are many different types of marker detection assays known in the art, it is not intended that the type of marker detection assay used to practice this invention be limited in any way.

Molecular Markers

"Marker," "genetic marker," "molecular marker," "marker nucleic acid," and "marker locus" refer to a nucleotide sequence or encoded product thereof (e.g., a protein) used as a point of reference when identifying a linked locus. A marker can be derived from genomic nucleotide sequence or from expressed nucleotide sequences (e.g., from a spliced RNA, a cDNA, etc.), or from an encoded polypeptide, and can be represented by one or more particular variant sequences, or by a consensus sequence. In another sense, a marker is an isolated variant or consensus of such a sequence. The term also refers to nucleic acid sequences complementary to or flanking the marker sequences, such as nucleic acids used as probes or primer pairs capable of amplifying the marker sequence. A "marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. A "marker locus" is a locus that can be used to track the presence of a second linked locus, e.g., a linked locus that encodes or contributes to expression of a phenotypic trait. For example, a marker locus can be used to monitor segregation of alleles at a locus, such as a QTL, that are genetically or physically linked to the marker locus. Thus, a "marker allele," alternatively an "allele of a marker locus" is one of a plurality of polymorphic nucleotide sequences found at a marker locus in a population that is polymorphic for the marker locus.

"Marker" also refers to nucleic acid sequences complementary to the genomic sequences, such as nucleic acids used as probes. Markers corresponding to genetic polymorphisms between members of a population can be detected by methods well-established in the art. These include, e.g., PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also known for the detection of expressed sequence tags (ESTs) and SSR markers derived from EST sequences and randomly amplified polymorphic DNA (RAPD).

A favorable allele of a marker is the allele of the marker that co-segregates with a desired phenotype (e.g., female gender skew). As used herein, a QTL marker has a minimum of one favorable allele, although it is possible that the marker might have two or more favorable alleles found in the population. Any favorable allele of that marker can be used advantageously for the identification and construction of plant lines having the desired phenotype. Optionally, one, two, three or more favorable allele(s) of different markers are identified in, or introgressed into a plant, and can be selected for or against during MAS. Desirably, plants or germplasm are identified that have at least one such favorable allele that positively correlates with female gender skew. Alternatively, a marker allele that co-segregates with gender skew also finds use with the invention, since that allele can be used to identify and counter select this trait in plants. Such an allele can be used for exclusionary purposes during breeding to identify alleles that negatively correlate with gender skew, to eliminate plants or germplasm having undesirable phenotypes from subsequent rounds of breeding.

The more tightly linked a marker is with a DNA locus influencing a phenotype, the more reliable the marker is in MAS, as the likelihood of a recombination event unlinking the marker and the locus decreases. Markers containing the causal mutation for a trait, or that are within the coding sequence of a causative gene, are ideal as no recombination is expected between them and the sequence of DNA responsible for the phenotype.

Genetic markers are distinguishable from each other (as well as from the plurality of alleles of any one particular marker) on the basis of polynucleotide length and/or sequence. In general, any differentially inherited polymorphic trait (including a nucleic acid polymorphism) that segregates among progeny is a potential genetic marker.

In some embodiments of the invention, one or more marker alleles are selected for in a single plant or a population of plants. In these methods, plants are selected that contain favorable alleles from more than one marker, or alternatively, favorable alleles from more than one marker are introgressed into a desired germplasm. One of skill recognizes that the identification of favorable marker alleles is germplasm-specific. The determination of which marker alleles correlate with female gender skew is determined for the particular germplasm under study. One of skill recognizes that methods for identifying the favorable alleles are routine and well known in the art, and furthermore, that the identification and use of such favorable alleles is well within the scope of this invention. Identification of favorable marker alleles in plant populations other than the populations used or described herein is well within the scope of this invention.

Marker Detection

In some aspects, methods of the invention utilize an amplification step to detect/genotype a marker locus, but amplification is not always a requirement for marker detection (e.g. Southern blotting and RFLP detection). Separate detection probes can also be omitted in amplification/detection methods, e.g., by performing a real time amplification reaction that detects product formation by modification of the relevant amplification primer upon incorporation into a product, incorporation of labeled nucleotides into an amplicon, or by monitoring changes in molecular rotation properties of amplicons as compared to unamplified precursors (e.g., by fluorescence polarization).

"Amplifying," in the context of nucleic acid amplification, is any process whereby additional copies of a selected nucleic acid (or a transcribed form thereof) are produced. In some embodiments, an amplification-based marker technology is used wherein a primer or amplification primer pair is admixed with genomic nucleic acid isolated from the first plant or germplasm, and wherein the primer or primer pair is complementary or partially complementary to at least a portion of the marker locus, and is capable of initiating DNA polymerization by a DNA polymerase using the plant genomic nucleic acid as a template. The primer or primer pair is extended in a DNA polymerization reaction having a DNA polymerase and a template genomic nucleic acid to generate at least one amplicon. In other embodiments, plant RNA is the template for the amplification reaction. In some embodiments, the QTL marker is a SNP type marker, and the detected allele is a SNP allele, and the method of detection is allele specific hybridization (ASH).

In general, the majority of genetic markers rely on one or more properties of nucleic acids for their detection. Typical amplification methods include various polymerase based replication methods, including the polymerase chain reaction (PCR), ligase mediated methods such as the ligase chain reaction (LCR) and RNA polymerase based amplification (e.g., by transcription) methods. An "amplicon" is an amplified nucleic acid, e.g., a nucleic acid that is produced by amplifying a template nucleic acid by any available amplification method (e.g., PCR, LCR, transcription, or the like). A "genomic nucleic acid" is a nucleic acid that corresponds in sequence to a heritable nucleic acid in a cell. Common examples include nuclear genomic DNA and amplicons thereof. A genomic nucleic acid is, in some cases, different from a spliced RNA, or a corresponding cDNA, in that the spliced RNA or cDNA is processed, e.g., by the splicing machinery, to remove introns. Genomic nucleic acids optionally comprise non-transcribed (e.g., chromosome structural sequences, promoter regions, enhancer regions, etc.) and/or non-translated sequences (e.g., introns), whereas spliced RNA/cDNA typically do not have non-transcribed sequences or introns. A "template nucleic acid" is a nucleic acid that serves as a template in an amplification reaction (e.g., a polymerase based amplification reaction such as PCR, a ligase mediated amplification reaction such as LCR, a transcription reaction, or the like). A template nucleic acid can be genomic in origin, or alternatively, can be derived from expressed sequences, e.g., a cDNA or an EST. Details regarding the use of these and other amplification methods can be found in any of a variety of standard texts. Many available biology texts also have extended discussions regarding PCR and related amplification methods and one of skill will appreciate that essentially any RNA can be converted into a double stranded DNA suitable for restriction digestion, PCR expansion and sequencing using reverse transcriptase and a polymerase.

PCR detection and quantification using dual-labeled fluorogenic oligonucleotide probes, commonly referred to as "TaqMan™" probes, can also be performed according to the present invention. These probes are composed of short (e.g., 20-25 base) oligodeoxynucleotides that are labeled with two different fluorescent dyes. On the 5' terminus of each probe is a reporter dye, and on the 3' terminus of each probe a quenching dye is found. The oligonucleotide probe sequence is complementary to an internal target sequence present in a PCR amplicon. When the probe is intact, energy transfer occurs between the two fluorophores and emission from the reporter is quenched by the quencher by FRET. During the extension phase of PCR, the probe is cleaved by 5' nuclease activity of the polymerase used in the reaction, thereby releasing the reporter from the oligonucleotide-quencher and producing an increase in reporter emission intensity. TaqMan™ probes are oligonucleotides that have a label and a quencher, where the label is released during amplification by the exonuclease action of the polymerase used in amplification, providing a real time measure of amplification during synthesis. A variety of TaqMan™ reagents are commercially available, e.g., from Applied Biosystems as well as from a variety of specialty vendors such as Biosearch Technologies.

In one embodiment, the presence or absence of a molecular marker is determined simply through nucleotide sequencing of the polymorphic marker region. This method is readily adapted to high throughput analysis as are the other methods noted above, e.g., using available high throughput sequencing methods such as sequencing by hybridization.

In alternative embodiments, in silico methods can be used to detect the marker loci of interest. For example, the sequence of a nucleic acid comprising the marker locus of interest can be stored in a computer. The desired marker locus sequence or its homolog can be identified using an appropriate nucleic acid search algorithm as provided by, for example, in such readily available programs as BLAST®, or even simple word processors.

While the exemplary markers provided in the tables herein are SNP markers, any of the aforementioned marker types can be employed in the context of the invention to identify chromosome intervals encompassing genetic element that contribute to female gender skew.

Probes and Primers

In general, synthetic methods for making oligonucleotides, including probes, primers, molecular beacons, PNAs, LNAs (locked nucleic acids), etc., are well known. For example, oligonucleotides can be synthesized chemically according to the solid phase phosphoramidite triester method described. Oligonucleotides, including modified oligonucleotides, can also be ordered from a variety of commercial sources.

Nucleic acid probes to the marker loci can be cloned and/or synthesized. Any suitable label can be used with a probe of the invention. Detectable labels suitable for use with nucleic acid probes include, for example, any composition detectable by spectroscopic, radioisotopic, photochemical, biochemical, immunochemical, electrical, optical or chemical means. Useful labels include biotin for staining with labeled streptavidin conjugate, magnetic beads, fluorescent dyes, radio labels, enzymes, and colorimetric labels. Other labels include ligands which bind to antibodies labeled with fluorophores, chemiluminescent agents, and enzymes. A probe can also constitute radio labeled PCR primers that are used to generate a radio labeled amplicon. It is not intended that the nucleic acid probes of the invention be limited to any particular size.

In some embodiments, the molecular markers of the invention are detected using a suitable PCR-based detection method, where the size or sequence of the PCR amplicon is indicative of the absence or presence of the marker (e.g., a particular marker allele). In these types of methods, PCR primers are hybridized to the conserved regions flanking the polymorphic marker region. As used in the art, PCR primers used to amplify a molecular marker are sometimes termed "PCR markers" or simply "markers." It will be appreciated that, although many specific examples of primers are provided herein, suitable primers to be used with the invention can be designed using any suitable method. It is not intended that the invention be limited to any particular primer or primer pair. In some embodiments, the primers of the invention are radiolabelled, or labeled by any suitable means (e.g., using a non-radioactive fluorescent tag), to allow for rapid visualization of the different size amplicons following an amplification reaction without any additional labeling step or visualization step. In some embodiments, the primers are not labeled, and the amplicons are visualized following their size resolution, e.g., following agarose gel electrophoresis. In some embodiments, ethidium bromide staining of the PCR amplicons following size resolution allows visualization of the different size amplicons. It is not intended that the primers of the invention be limited to generating an amplicon of any particular size. For example, the primers used to amplify the marker loci and alleles herein are not limited to amplifying the entire region of the relevant locus. The primers can generate an amplicon of any suitable length that is longer or shorter than those disclosed herein. In some embodiments, marker amplification produces an amplicon at least 20 nucleotides in length, or alternatively, at least 50 nucleotides in length, or alternatively, at least 100 nucleotides in length, or alternatively, at least 200 nucleotides in length. Marker alleles in addition to those recited herein also find use with the present invention.

Linkage Analysis

"Linkage", or "genetic linkage," is used to describe the degree with which one marker locus is associated with another marker locus or some other locus (for example, a female gender skew locus). A marker locus may be located within a locus to which it is genetically linked. For example, if locus A has genes "A" or "a" and locus B has genes "B" or "b" and a cross between parent 1 with AABB and parent 2 with aabb will produce four possible gametes where the genes are segregated into AB, Ab, aB and ab. The null expectation is that there will be independent equal segregation into each of the four possible genotypes, i.e. with no linkage ¼ of the gametes will of each genotype. Segregation of gametes into a genotypes differing from ¼ is attributed to linkage. As used herein, linkage can be between two markers, or alternatively between a marker and a phenotype. A marker locus may be genetically linked to a trait, and in some cases a marker locus genetically linked to a trait is located within the allele conferring the trait. A marker may also be causative for a trait or phenotype, for example a causative polymorphism. The degree of linkage of a molecular marker to a phenotypic trait (e.g., a QTL) is measured, e.g., as a statistical probability of co-segregation of that molecular marker with the phenotype.

As used herein, "closely linked" means that the marker or locus is within about 20 cM, for instance within about 10 cM, about 5 cM, about 1 cM, about 0.5 cM, or less than 0.5 cM of the identified locus associated with female gender skew.

As used herein, the linkage relationship between a molecular marker and a phenotype is given is the statistical likelihood that the particular combination of a phenotype and the presence or absence of a particular marker allele is random. Thus, the lower the probability score, the greater the likelihood that a phenotype and a particular marker will cosegregate. In some embodiments, a probability score of 0.05 (p=0.05, or a 5% probability) of random assortment is considered a significant indication of co-segregation. However, the present invention is not limited to this particular standard, and an acceptable probability can be any probability of less than 50% (p<0.5). For example, a significant probability can be less than 0.25, less than 0.20, less than 0.15, or less than 0.1. The phrase "closely linked," in the present application, means that recombination between two linked loci occurs with a frequency of equal to or less than about 10% (i.e., are separated on a genetic map by not more than 10 cM). In one aspect, any marker of the invention is linked (genetically and physically) to any other marker that is at or less than 50 cM distant. In another aspect, any marker of the invention is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

Classical linkage analysis can be thought of as a statistical description of the relative frequencies of cosegregation of different traits. Linkage analysis is the well characterized descriptive framework of how traits are grouped together based upon the frequency with which they segregate together. That is, if two non-allelic traits are inherited together with a greater than random frequency, they are said to be "linked." The frequency with which the traits are inherited together is the primary measure of how tightly the traits are linked, i.e., traits which are inherited together with a higher frequency are more closely linked than traits which are inherited together with lower (but still above random) frequency. The further apart on a chromosome the genes reside, the less likely they are to segregate together, because homologous chromosomes recombine during meiosis. Thus, the further apart on a chromosome the genes reside, the more likely it is that there will be a crossing over event during meiosis that will result in the marker and the DNA sequence responsible for the trait the marker is designed to track segregating separately into progeny. A common measure of linkage is the frequency with which traits cosegregate.

Linkage analysis is used to determine which polymorphic marker allele demonstrates a statistical likelihood of co-segregation with a desired gender skew phenotype (a "gender skew marker allele"). Following identification of a marker allele for co-segregation with the gender skew phenotype, it is possible to use this marker for rapid, accurate screening of plant lines for female gender skew alleles without the need to grow the plants through their life cycle and await phenotypic evaluations, and furthermore, permits genetic selection for the particular allele even when the molecular identity of the actual gender skew QTL is unknown. Tissue samples can be taken, for example, from the endosperm, embryo, or mature/developing plant and screened with the appropriate molecular marker to rapidly determine determined which progeny contain the desired genetics. Linked markers also remove the impact of environmental factors that can often influence phenotypic expression.

Because chromosomal distance is approximately proportional to the frequency of crossing over events between traits, there is an approximate physical distance that correlates with recombination frequency. Marker loci are themselves traits and can be assessed according to standard linkage analysis by tracking the marker loci during segregation. Thus, in the context of the present invention, one cM is equal to a 1% chance that a marker locus will be separated from another locus (which can be any other trait, e.g., another marker locus, or another trait locus that encodes a QTL), due to crossing over in a single generation.

When referring to the relationship between two genetic elements, such as a genetic element contributing to gender skew and a proximal marker, "coupling" phase linkage indicates the state where the "favorable" allele at the female gender skew locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest (e.g., a QTL for gender skew) is physically linked with an "unfavorable" allele at the proximal marker locus, and the two "favorable" alleles are not inherited together (i.e., the two loci are "out of phase" with each other).

Genetic Mapping

A "genetic map" is the relationship of genetic linkage among loci on one or more chromosomes (or linkage groups) within a given species, generally depicted in a diagrammatic or tabular form. "Genetic mapping" is the process of defining the linkage relationships of loci through the use of genetic markers, populations segregating for the markers, and standard genetic principles of recombination frequency. A "genetic map location" is a location on a genetic map relative to surrounding genetic markers on the same linkage group where a specified marker can be found within a given species. In contrast, a physical map of the genome refers to absolute distances (for example, measured in base pairs or isolated and overlapping contiguous genetic fragments, e.g., contigs). A physical map of the genome does not take into account the genetic behavior (e.g., recombination frequencies) between different points on the physical map. A "genetic recombination frequency" is the frequency of a crossing over event (recombination) between two genetic loci. Recombination frequency can be observed by following the segregation of markers and/or traits following meiosis. In some cases, two different markers can have the same genetic map coordinates. In that case, the two markers are in such close proximity to each other that recombination occurs between them with such low frequency that it is undetected.

Genetic maps are graphical representations of genomes (or a portion of a genome such as a single chromosome) where the distances between markers are measured by the recombination frequencies between them. Plant breeders use genetic maps of molecular markers to increase breeding efficiency through MAS, a process where selection for a trait of interest is not based on the trait itself but rather on the genotype of a marker linked to the trait. A molecular marker that demonstrates reliable linkage with a phenotypic trait provides a useful tool for indirectly selecting the trait in a plant population, especially when accurate phenotyping is difficult, slow, or expensive.

In general, the closer two markers or genomic loci are on the genetic map, the closer they lie to one another on the physical map. A lack of precise proportionality between cM distances and physical distances can exist due to the fact that the likelihood of genetic recombination is not uniform throughout the genome; some chromosome regions are cross-over "hot spots," while other regions demonstrate only rare recombination events, if any.

Genetic mapping variability can also be observed between different populations of the same crop species. In spite of this variability in the genetic map that may occur between populations, genetic map and marker information derived from one population generally remains useful across multiple populations in identification of plants with desired traits, counter-selection of plants with undesirable traits and in guiding MAS.

As one of skill in the art will recognize, recombination frequencies (and as a result, genetic map positions) in any particular population are not static. The genetic distances separating two markers (or a marker and a QTL) can vary depending on how the map positions are determined. For example, variables such as the parental mapping populations used, the software used in the marker mapping or QTL mapping, and the parameters input by the user of the mapping software can contribute to the QTL marker genetic map relationships. However, it is not intended that the invention be limited to any particular mapping populations, use of any particular software, or any particular set of software parameters to determine linkage of a particular marker or chromosome interval with a desired phenotype. It is well within the ability of one of ordinary skill in the art to extrapolate the novel features described herein to any gene pool or population of interest, and using any particular software and software parameters. Indeed, observations regarding genetic markers and chromosome intervals in populations in addition to those described herein are readily made using the teaching of the present disclosure.

Association Mapping

Association or LD mapping techniques aim to identify genotype-phenotype associations that are significant. It is effective for fine mapping in outcrossing species where frequent recombination among heterozygotes can result in rapid LD decay. LD is non-random association of alleles in a collection of individuals, reflecting the recombinational history of that region. Thus, LD decay averages can help determine the number of markers necessary for a genome-wide association study to generate a genetic map with a desired level of resolution.

Large populations are better for detecting recombination, while older populations are generally associated with higher levels of polymorphism, both of which contribute to accelerated LD decay. However, smaller effective population sizes tend to show slower LD decay, which can result in more extensive haplotype conservation. Understanding of the relationships between polymorphism and recombination is useful in developing strategies for efficiently extracting information from these resources. Association analyses compare the plants' phenotypic score with the genotypes at the various loci. Subsequently, any suitable maize genetic map (for example, a composite map) can be used to help observe distribution of the identified QTL markers and/or QTL marker clustering using previously determined map locations of the markers.

Marker Assisted Selection

"Introgression" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, a transgene, or the like. In any case, offspring comprising the desired allele can be repeatedly backcrossed to a line having a desired genetic background and selected for the desired allele, to result in the allele becoming fixed in a selected genetic background.

A primary motivation for development of molecular markers in crop species is the potential for increased efficiency in plant breeding through MAS. Genetic markers are used to identify plants that contain a desired genotype at one or more loci, and that are expected to transfer the desired genotype, along with a desired phenotype to their progeny. Genetic markers can be used to identify plants containing a desired genotype at one locus, or at several unlinked or linked loci (e.g., a haplotype), and that would be expected to transfer the desired genotype, along with a desired phenotype to their progeny. The present invention provides the means to identify plants that exhibit female gender skew by identifying plants having a specified allele that is linked to the gender skew locus on chromosome 4.

In general, MAS uses polymorphic markers that have been identified as having a significant likelihood of co-segregation with a desired trait. Such markers are presumed to map near a gene or genes that give the plant its desired phenotype, and are considered indicators for the desired trait, and are termed QTL markers. Plants are tested for the presence or absence of a desired allele in the QTL marker.

Identification of plants or germplasm that include a marker locus or marker loci linked to a desired trait or traits provides a basis for performing MAS. Plants that comprise favorable markers or favorable alleles are selected for, while plants that comprise markers or alleles that are negatively correlated with the desired trait can be selected against. Desired markers and/or alleles can be introgressed into plants having a desired (e.g., elite or exotic) genetic background to produce an introgressed plant or germplasm having the desired trait. In some aspects, it is contemplated that a plurality of markers for desired traits are sequentially or simultaneous selected and/or introgressed. The combinations of markers that are selected for in a single plant is not limited, and can include any combination of markers disclosed herein or any marker linked to the markers disclosed herein, or any markers located within the QTL intervals defined herein.

In some embodiments, a first *Cannabis* plant or germplasm exhibiting a desired trait (the donor) can be crossed with a second *Cannabis* plant or germplasm (the recipient, e.g., an elite or exotic *Cannabis*, depending on characteristics that are desired in the progeny) to create an introgressed *Cannabis* plant or germplasm as part of a breeding program. In some aspects, the recipient plant can also contain one or more loci associated with one or more desired traits, which can be qualitative or quantitative trait loci. In another aspect, the recipient plant can contain a transgene.

In some embodiments, the recipient *Cannabis* plant or germplasm will typically display less desirable gender skew as compared to the first *Cannabis* plant or germplasm, while the introgressed *Cannabis* plant or germplasm will exhibit female gender skew as compared to the second plant or germplasm. An introgressed *Cannabis* plant or germplasm produced by these methods are also a feature of this invention.

MAS is a powerful shortcut to selecting for desired phenotypes and for introgressing desired traits into cultivars (e.g., introgressing desired traits into elite lines). MAS is easily adapted to high throughput molecular analysis methods that can quickly screen large numbers of plant or germplasm genetic material for the markers of interest and is much more cost effective than raising and observing plants for visible traits.

When a population is segregating for multiple loci affecting one of multiple traits, e.g., multiple loci involved in gender skew, the efficiency of MAS compared to phenotypic screening becomes even greater, because all of the loci can be evaluated in the lab together from a single sample of DNA.

Introgression of Gender Skew Loci Using MAS

The introgression of one or more desired loci from a donor line into another is achieved via repeated backcrossing to a recurrent parent accompanied by selection to retain one or more loci from the donor parent. Markers associated with female gender skew are assayed in progeny and those progeny with one or more desired markers are selected for advancement. In another aspect, one or more markers can be assayed in the progeny to select for plants with the genotype of the elite parent. This invention anticipates that trait introgression activities will require more than one generation, wherein progeny are crossed to the recurrent (elite) parent or selfed. Selections are made based on the presence of one or more female gender skew markers and can also be made based on the recurrent parent genotype, wherein screening is performed on a genetic marker and/or phenotype basis. In another embodiment, markers of this invention can be used in conjunction with other markers, ideally at least one on each chromosome of the *Cannabis* genome, to track the introgression of female gender skew loci into elite germplasm. It is within the scope of this invention to utilize the methods and compositions for trait integration of female gender skew. It is contemplated by the inventors that the present invention will be useful for developing commercial varieties with female gender skew and an elite phenotype.

In one aspect, this invention could be used on any plant. In another aspect, the plant is selected from the genus *Cannabis*. In another aspect, the plant is selected from the species *Cannabis sativa*. In a further aspect, the plant is selected from the species *Cannabis sativa* forma indica, otherwise known as *Cannabis* indica. In an additional aspect, the plant is selected from the species *Cannabis ruderalis*.

In another aspect, a *Cannabis* plant of the invention can show a gender skew toward female plants compared to a control *Cannabis* plant. In this aspect, a control *Cannabis* plant will preferably be genetically similar except for the gender skew allele or alleles in question.

Further Embodiments of the Invention

This invention is also directed to methods for producing a *Cannabis* plant by crossing a first parent *Cannabis* plant with a second parent *Cannabis* plant, wherein the first parent *Cannabis* plant or second parent *Cannabis* plant is the *Cannabis* plant from cultivar NWG28. Further, both the first parent *Cannabis* plant and second parent *Cannabis* plant may be from cultivar NWG28. Therefore, any methods using hemp *Cannabis* cultivar NWG28 are part of this invention, such as selfing, backcrosses, hybrid breeding, and crosses to populations. Plants produced using hemp *Cannabis* cultivar NWG28 as at least one parent are within the scope of this invention.

In one aspect of the invention, methods for developing novel plant types are presented. In one embodiment the specific type of breeding method is pedigree selection, where both single plant selection and mass selection practices are employed. Pedigree selection, also known as the "Vilmorin system of selection," is described in Fehr, Walter; Principles of Cultivar Development, Volume I, Macmillan Publishing Co., which is hereby incorporated by reference.

In one embodiment, the pedigree method of breeding is practiced where selection is first practiced among $F_2$ plants. In the next season, the most desirable $F_3$ lines are first identified, and then desirable $F_3$ plants within each line are selected. The following season and in all subsequent generations of inbreeding, the most desirable families are identified first, then desirable lines within the selected families are chosen, and finally desirable plants within selected lines are harvested individually. A family refers to lines that were derived from plants selected from the same progeny row the preceding generation.

Using this pedigree method, two parents may be crossed using an emasculated female and a pollen donor (male) to produce $F_1$ offspring. The $F_1$ may be self-pollinated to produce a segregating $F_2$ generation. Individual plants may then be selected which represent the desired phenotype in each generation ($F_3$, $F_4$, $F_5$, etc.) until the traits are homozygous or fixed within a breeding population.

In addition to crossing, selection may be used to identify and isolate new *Cannabis* lines. In *Cannabis* selection, *Cannabis* seeds are planted, the plants are grown and single plant selections are made of plants with desired characteristics. Seed from the single plant selections may be harvested, separated from seeds of the other plants in the field and re-planted. The plants from the selected seed may be monitored to determine if they exhibit the desired characteristics of the originally selected line. Selection work is preferably continued over multiple generations to increase the uniformity of the new line.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding may be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program may include a periodic, objective evaluation of the efficiency of the breeding procedure. Evaluation criteria vary depending on the goal and objectives, but should include gain from selection per year based on comparisons to an appropriate standard, the overall value of the advanced breeding lines, and the number of successful cultivars produced per unit of input (e.g., per year, per dollar expended, etc.).

In one embodiment, promising advanced breeding lines are thoroughly tested and compared to appropriate standards in environments representative of the commercial target area(s). The best lines are candidates for new commercial cultivars; those still deficient in a few traits are used as parents to produce new populations for further selection.

These processes, which lead to the final step of marketing and distribution, usually take several years from the time the first cross or selection is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of *Cannabis* plant breeding is to develop new, unique and superior *Cannabis* cultivars. In one embodiment, the breeder initially selects and crosses two or more parental lines, followed by repeated selfing and selection, producing many new genetic combinations. The breeder can theoretically generate billions of different genetic combinations via crossing, selfing and mutations. Preferably, each year the plant breeder selects the germplasm to advance to the next generation. This germplasm may be grown under different geographical, climatic and soil conditions, and further selections are then made, during and at the end of the growing season.

In a preferred embodiment, the development of commercial *Cannabis* cultivars requires the development of *Cannabis* varieties, the crossing of these varieties, and the evaluation of the crosses. Pedigree breeding and recurrent selection breeding methods may be used to develop cultivars from breeding populations. Breeding programs may combine desirable traits from two or more varieties or various broad-based sources into breeding pools from which cultivars are developed by selfing and selection of desired phenotypes. The new cultivars may be crossed with other varieties and the hybrids from these crosses are evaluated to determine which have commercial potential.

Pedigree breeding is used commonly for the improvement of self-pollinating crops or inbred lines of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population; then, beginning in the $F_3$, the best individuals in the best families are usually selected. Replicated testing of families, or hybrid combinations involving individuals of these families, often follows in the $F_4$ generation to improve the effectiveness of selection for traits with low heritability. At an advanced stage of inbreeding (e.g., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals may be identified or created by intercrossing several different parents. The best plants may be selected based on individual superiority, outstanding progeny, or excellent combining ability. Preferably, the selected plants are intercrossed to produce a new population in which further cycles of selection are continued.

Backcross breeding has been used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent may be selected and repeatedly crossed (backcrossed) to the recurrent parent. The resulting plant is expected to have the attributes of the recurrent parent (e.g., cultivar) and the desirable trait transferred from the donor parent.

The single-seed descent procedure refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs).

Isozyme Electrophoresis and RFLPs have been widely used to determine genetic composition. Shoemaker and Olsen, (Molecular Linkage Map of Soybean (*Glycine max*) p 6.131-6.138 in S. J. O'Brien (ed) Genetic Maps: Locus Maps of Complex Genomes, Cold Spring Harbor Laboratory Press, Cold Spring Harbor, N.Y., (1993)) developed a molecular genetic linkage map that consisted of 25 linkage groups with about 365 RFLP, 11 RAPD, three classical markers and four isozyme loci. See also, Shoemaker, R. C., RFLP Map of Soybean, p 299-309, in Phillips, R. L. and Vasil, I. K., eds. DNA-Based Markers in Plants, Kluwer Academic Press, Dordrecht, the Netherlands (1994).

SSR technology is currently the most efficient and practical marker technology; more marker loci can be routinely used and more alleles per marker locus can be found using SSRs in comparison to RFLPs. For example, Diwan and Cregan described a highly polymorphic microsatellite locus in soybean with as many as 26 alleles. (Diwan, N. and Cregan, P. B., Theor. Appl. Genet. 95:22-225, 1997.) SNPs may also be used to identify the unique genetic composition of the invention and progeny varieties retaining that unique genetic composition. Various molecular marker techniques may be used in combination to enhance overall resolution.

Molecular markers, which include markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the identification of markers which are closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding is another method of introducing new traits into Cannabis varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding can be found in Principles of Cultivar Development by Fehr, Macmillan Publishing Company, 1993.

The production of double haploids can also be used for the development of homozygous varieties in a breeding program. Double haploids are produced by the doubling of a set of chromosomes from a heterozygous plant to produce a completely homozygous individual. For example, see Wan et al., Theor. Appl. Genet., 77:889-892, 1989.

Descriptions of other breeding methods that are commonly used for different traits and crops can be found in one of several reference books (e.g., Principles of Plant Breeding John Wiley and Son, pp. 115-161, 1960; Allard, 1960; Simmonds, 1979; Sneep et al., 1979; Fehr, 1987; "Carrots and Related Vegetable Umbelliferae", Rubatzky, V. E., et al., 1999).

Cannabis is an important and valuable crop. Thus, a continuing goal of Cannabis plant breeders is to develop stable, high yielding Cannabis cultivars that are agronomically sound. To accomplish this goal, the Cannabis breeder preferably selects and develops Cannabis plants with traits that result in superior cultivars.

This invention also is directed to methods for producing a Cannabis cultivar plant by crossing a first parent Cannabis plant with a second parent Cannabis plant wherein either the first or second parent Cannabis plant is a Cannabis plant of the line NWG28. Further, both first and second parent Cannabis plants can come from the cultivar NWG28. Still further, this invention also is directed to methods for producing a cultivar NWG28-derived Cannabis plant by crossing cultivar NWG28 with a second Cannabis plant and growing the progeny seed, and repeating the crossing and growing steps with the cultivar NWG28-derived plant from 0 to 7 times. Thus, any such methods using the cultivar NWG28 are part of this invention: selfing, backcrosses, hybrid production, crosses to populations, and the like. All plants produced using cultivar NWG28 as a parent are within the scope of this invention, including plants derived from cultivar NWG28. Advantageously, the cultivar is used in crosses with other, different, cultivars to produce first generation ($F_1$) Cannabis seeds and plants with superior characteristics.

As used herein, the term plant includes plant cells, plant protoplasts, plant cell tissue cultures from which Cannabis plants can be regenerated, plant calli, plant clumps and plant cells that are intact in plants or parts of plants, such as embryos, pollen, ovules, flowers, seeds, roots, anthers, and the like.

As is well known in the art, tissue culture of Cannabis can be used for the in vitro regeneration of a Cannabis plant. Tissue culture of various tissues of Cannabis and regeneration of plants therefrom is well known and widely published. For example, reference may be had to Teng et al., HortScience. 1992, 27: 9, 1030-1032 Teng et al., HortScience. 1993, 28: 6, 669-1671, Zhang et al., Journal of Genetics and Breeding. 1992, 46: 3, 287-290, Webb et al., Plant Cell Tissue and Organ Culture. 1994, 38: 1, 77-79, Curtis et al., Journal of Experimental Botany. 1994, 45: 279, 1441-1449, Nagata et al., Journal for the American Society for Horticultural Science. 2000, 125: 6, 669-672. It is clear from the literature that the state of the art is such that these methods of obtaining plants are, and were, "conventional" in the sense that they are routinely used and have a very high rate of success. Thus, another aspect of this invention is to provide cells which upon growth and differentiation produce Cannabis plants having the physiological and morphological characteristics of variety NWG28.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as transgenes. Over the last fifteen to twenty years several methods for producing transgenic plants have been developed, and the present invention, in particular embodiments, also relates to transformed versions of the claimed line.

Plant transformation preferably involves the construction of an expression vector that will function in plant cells. Such a vector may comprise DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed Cannabis plants, using transformation methods as described below to incorporate transgenes into the genetic material of the Cannabis plant(s).

Expression Vectors for Cannabis Transformation

Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley et al., Proc. Natl. Acad. Sci. U.S.A., 80:4803 (1983). Another commonly used selectable marker gene is the hygromycin phosphotransferase gene which confers resistance to the antibiotic hygromycin. Vanden Elzen et al., Plant Mol. Biol., 5:299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford et al., Plant Physiol. 86:1216 (1988), Jones et al., Mol. Gen. Genet., 210:86 (1987), Svab et al., Plant Mol. Biol. 14:197 (1990<Hille et al., Plant Mol. Biol. 7:171 (1986). Other selectable marker genes confer resistance to herbicides such as glyphosate, glufosinate or broxynil. Comai et al., Nature 317:741-744 (1985), Gordon-Kamm et al., Plant Cell 2:603-618 (1990) and Stalker et al., Science 242:419-423 (1988).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., Somatic Cell Mol. Genet. 13:67 (1987), Shah et al., Science 233:478 (1986), Charest et al., Plant Cell Rep. 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include beta.-glucuronidase (GUS), .beta.-galaetesidase, luciferase and chloramphenicol, acetyltransferase. Jefferson, R. A., Plant Mol. Biol. Rep. 5:387 (1987), Teen et al., EMBO J. 8:343 (1989), Koncz et al., Proc. Natl. Acad. Sci U.S.A. 84:131 (1987), DeBlock et al., EMBO J. 3:1681 (1984).

Recently, in vivo methods for visualizing GUS activity that do not require destruction of plant tissue have been made available. Molecular Probes publication 2908, Imagene Green™, p. 1-4 (1993) and Naleway et al., J. Cell Biol. 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., Science 263:802 (1994). GFP and mutants of GFP may be used as screenable markers.

Promoters

Genes included in expression vectors preferably are driven by nucleotide sequence comprising a regulatory element, for example, a promoter. Several types of promoters are now well known in the transformation arts, as are other regulatory elements that can be used alone or in combination with promoters.

As used herein, promoter includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may affect transcription by inducible promoters include anaerobic conditions or the presence of light. Tissue-specific, tissue-preferred, cell type specific, and inducible promoters constitute the class of "non-constitutive" promoters. A "constitutive promoter" is a promoter which is active under most environmental conditions.

A. Inducible Promoters

An inducible promoter is operably linked to a gene for expression in *Cannabis*. Optionally, the inducible promoter is operably linked to a nucleotide sequence encoding a signal sequence which is operably linked to a gene for expression in *Cannabis*. With an inducible promoter the rate of transcription increases in response to an inducing agent. Any inducible promoter can be used in the instant invention. See Ward et al., Plant Mol. Biol. 22:361-366 (1993). Exemplary inducible promoters include, but are not limited to, that from the ACEI system which responds to copper (Meft et al., PNAS 90:4567-4571 (1993)); In2 gene from maize which responds to benzenesulfonamide herbicide safeners (Hershey et al., Mol. Gen Genetics 227:229-237 (1991) and Gatz et al., Mol. Gen. Genetics 243:32-38 (1994)) or Tet repressor from Tn10 (Gatz et al., Mol. Gen. Genetics 227:229-237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., Proc. Natl. Acad. Sci. U.S.A. 88:0421 (1991).

B. Constitutive Promoters

A constitutive promoter may be operably linked to a gene for expression in *Cannabis* or the constitutive promoter may operably linked to a nucleotide sequence encoding a signal sequence which is operably linked to a gene for expression in *Cannabis*.

Many different constitutive promoters can be utilized in the instant invention. Exemplary constitutive promoters include, but are not limited to, the promoters from plant viruses such as the 35S promoter from CaMV (Odell et al., Nature 313:810-812 (1985) and the promoters from such genes as rice actin (McElroy et al., Plant Cell 2:163-171 (1990)); ubiquitin (Christensen et al., Plant Mol. Biol. 12:619-632 (1989) and Christensen et al., Plant Mol. Biol. 18:675-689 (1992)); pEMU (Last et al., Theor. Appl. Genet.

81:581-588 (1991)); MAS (Velten et al., EMBO J. 3:2723-2730 (1984)) and maize H3 histone (Lepetit et al., Mol. Gen. Genetics 231:276-285 (1992) and Atanassova et al., Plant Journal 2 (3): 291-300 (1992)). The ALS promoter, Xbal/Ncol fragment 5' to the *Brassica napus* ALS3 structural gene (or a nucleotide sequence similarity to said Xbal/Ncol fragment), represents a particularly useful constitutive promoter. See PCT application WO96/30530.

C. Tissue-Specific or Tissue Preferred Promoters

A tissue-specific promoter may be operably linked to a gene for expression in *Cannabis*. Optionally, the tissue-specific promoter is operably linked to a nucleotide sequence encoding a signal sequence which is operably linked to a gene for expression in *Cannabis*. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., Science 23:476-482 (1983) and Sengupta-Gopalan et al., Proc. Natl. Acad. Sci. U.S.A. 82:3320-3324 (1985)); a leaf-specific and light-induced promoter such as that from cab or rubisco (Simpson et al., EMBO J. 4(11):2723-2729 (1985) and Timko et al., Nature 318:579-582 (1985)); an anther-specific promoter such as that from LAT52 (Twell et al., Mol. Gen. Genetics 217:240-245 (1989)); a pollen-specific promoter such as that from Zm13 (Guerrero et al., Mol. Gen. Genetics 244:161-168 (1993)) or a microspore-preferred promoter such as that from apg (Twell et al., Sex. Plant Reprod. 6:217-224 (1993).

Signal Sequences for Targeting Proteins to Subcellular Compartments

Transport of protein produced by transgenes to a subcellular compartment such as the chloroplast, vacuole, peroxisome, glyoxysome, cell wall or mitochondroin or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., Plant Mol. Biol. 20:49 (1992), Close, P. S., Master's Thesis, Iowa State University (1993), Knox, C., et al., Structure and Organization of Two Divergent Alpha-Amylase Genes from Barley, Plant Mol. Biol. 9:3-17 (1987), Lerner et al., Plant Physiol. 91:124-129 (1989), Fontes et al., Plant Cell 3:483-496 (1991), Matsuoka et al., Proc. Natl. Acad. Sci. 88:834 (1991), Gould et al., J. Cell. Biol. 108:1657 (1989), Creissen et al., Plant J. 2:129 (1991), Kalderon, et al., A short amino acid sequence able to specify nuclear location, Cell 39:499-509 (1984), Steifel, et al., Expression of a maize cell wall hydroxyproline-rich glycoprotein gene in early leaf and root vascular differentiation, Plant Cell 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants that are harvested in a conventional manner, and a foreign protein then can be extracted from a tissue of interest or from total biomass. Protein extraction from plant biomass can be accomplished by known methods which are discussed, for example, by Heney and Orr, Anal. Biochem. 114:92-6 (1981).

According to a preferred embodiment, the transgenic plant provided for commercial production of foreign protein is *Cannabis*. In another preferred embodiment, the biomass of interest is seed. For transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant.

Map comparisons may involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant line can be transformed with cloned resistance gene to engineer plants that are resistant to specific pathogen strains. See, for example Jones et al., Science 266:789 (1994) (cloning of the tomato Cf-9 gene for resistance to *Cladosporium fulvum*); Martin et al., Science 262:1432 (1993) (tomato Pto gene for resistance to *Pseudomonas syringae* pv. Tomato encodes a protein kinase); Mindrinos et al., Cell 78:1089 (1994) (*Arabidopsis* RSP2 gene for resistance to *Pseudomonas syringae*).

B. A *Bacillus thuringiensis* protein, a derivative thereof or a synthetic polypeptide modeled thereon. See, for example, Geiser et al., Gene 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

C. A lectin. See, for example, the disclosure by Van Damme et al., Plant Molec. Biol. 24:25 (1994), who disclose the nucleotide sequences of several *Clivia miniata* mannose-binding lectin genes.

D. A vitamin-binding protein such as avidin. See PCT application US93/06487, the contents of which are hereby incorporated by reference. The application teaches the use of avidin and avidin homologues as larvicides against insect pests.

E. An enzyme inhibitor, for example, a protease or proteinase inhibitor or an amylase inhibitor. See, for example, Abe et al., J. Biol. Chem. 262:16793 (1987) (nucleotide sequence of rice cysteine proteinase inhibitor), Huub et al., Plant Molec. Biol. 21:985 (1993) (nucleotide sequence of cDNA encoding tobacco proteinase inhibitor I), Sumitani et al., Biosci. Biotoch. Biochem. 57:1243 (1993) (nucleotide sequence of *Streptomyces nitrosporeus* α-amylase inhibitor).

F. An insect-specific hormone or pheromone such as an ecdysteroid and juvenile hormone, a variant thereof, a mimetic based thereon, or an antagonist or agonist thereof. See, for example, the disclosure by Hammock et al., Nature 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, J. Biol. Chem. 269:9 (1994) (expression cloning yields DNA coding for insect diuretic hormone receptor), and Pratt et al., Biochem. Biophys. Res. Comm. 163:1243 (1989) (an allostatin is identified in *Diploptera puntata*). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., Gene 116:165 (1992), for disclosure of heterologous expression in plants of a gene coding for a scorpion insectotoxic peptide.

I. An enzyme responsible for a hyper accumulation of a monterpene, a sesquiterpene, a steroid, hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol. 23:691 (1993), who teach the nucleotide sequence of a cDNA encoding tobacco hookworm chitinase, and Kawalleck et al., Plant Molec. Biol. 21:673 (1993), who provide the nucleotide sequence of the parsley ubi4-2 polyubiquitin gene.

K. A molecule that stimulates signal transduction. For example, see the disclosure by Botella et al., Plant Molec. Biol. 24:757 (1994), of nucleotide sequences for mung *Cannabis* calmodulin cDNA clones, and Griess et al., Plant Physiol. 104:1467 (1994), who provide the nucleotide sequence of a maize calmodulin cDNA clone.

L. A hydrophobic moment peptide. See PCT application WO95/16776 (disclosure of peptide derivatives of tachyolesin which inhibit fungal plant pathogens) and PCT application WO95/18855 (teaches synthetic antimicrobial peptides that confer disease resistance), the respective contents of which are hereby incorporated by reference.

M. A membrane permease, a channel former or a channel blocker. For example, see the disclosure of Jaynes et al., Plant Sci 89:43 (1993), of heterologous expression of a cecropin-β, lytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. rev. Phytopathol. 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

O. An insect-specific antibody or an immunotoxin derived therefrom. Thus, an antibody targeted to a critical metabolic function in the insect gut would inactivate an affected enzyme, killing the insect. Cf Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

P. A virus-specific antibody. See, for example, Tavladoraki et al., Nature 366:469 (1993), who show that transgenic plants expressing recombinant antibody genes are protected from virus attack.

Q. A developmental-arrestive protein produced in nature by a pathogen or a parasite. Thus, fungal endo-α-1, 4-D-polygalacturonases facilitate fungal colonization and plant nutrient release by solubilizing plant cell wall homo-α-1, 4-D-galacturonase. See Lamb at al., Bio/Technology 10:1436 (1992). The cloning and characterization of a gene which encodes a *Cannabis* endopolygalacturonase-inhibiting protein is described by Toubart et al., Plant J. 2:367 (1992).

R. A development-arrestive protein produced in nature by a plant. For example, Logemann et al., Bioi/Technology 10:305 (1992), have shown that transgenic plants expressing the barley ribosome-inactivating gene have an increased resistance to fungal disease.

S. A *Cannabis* mosaic potyvirus (LMV) coat protein gene introduced into *Lactuca sativa* in order to increase its resistance to LMV infection. See Dinant et al., Molecular Breeding. 1997, 3: 1, 75-86.

2. Genes that Confer Resistance to an Herbicide, for Example:

A. A herbicide that inhibits the growing point or meristem, such as an imidazalinone or a sulfonylurea. Exemplary genes in this category code for mutant ALS and AHAS enzyme as described, for example, by Lee et al., EMBO J. 7:1241 (1988), and Miki et al., Theor. Appl. Genet. 80:449 (1990), respectively.

B. Glyphosate (resistance impaired by mutant 5-enolpyruvl-3-phosphikimate synthase (EPSP) and aroA genes, respectively) and other phosphono compounds such as glufosinate (phosphinothricin acetyl transferase, PAT and *Streptomyces hygroscopicus* phosphinothricin-acetyl transferase PAT bar genes), and pyridinoxy or phenoxy propionic acids and cycloshexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. See also Umaballava-Mobapathie in Transgenic Research. 1999, 8: 1, 33-44 that discloses *Lactuca sativa* resistant to glufosinate. European patent application No. 0 333 033 to Kumada at al., and U.S. Pat. No. 4,975,374 to Goodman et al., disclose nucleotide sequences of glutamine synthetase genes which confer resistance to herbicides such as L-phosphinothricin. The nucleotide sequence of a phosphinothricin-acetyl-transferase gene is provided in European application No. 0 242 246 to Leemans et al., DeGreef et al., Bio/Technology 7:61 (1989), describe the production of transgenic plants that express chimeric bar genes coding for phosphinothricin acetyl transferase activity. Exemplary of genes conferring resistance to phenoxy propionic acids and cycloshexones, such as sethoxydim and haloxyfop are the Accl-S1, Accl-S2 and Accl-S3 genes described by Marshall et al., Theor. Appl. Genet. 83:435 (1992).

C. A herbicide that inhibits photosynthesis, such as a triazine (psbA and gs+ genes) and a benzonitrile (nitrilase gene). Przibilla et al., Plant Cell 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., Biochem. J. 285:173 (1992).

D. Acetohydroxy acid synthase, which has been found to make plants that express this enzyme resistant to multiple types of herbicides, has been introduced into a variety of plants. See Hattori et al., Mol. Gen. Genet. 246:419, 1995. Other genes that confer tolerance to herbicides include a gene encoding a chimeric protein of rat cytochrome P4507A1 and yeast NADPH-cytochrome P450 oxidoreductase (Shiota et al., Plant Physiol., 106:17, 1994), genes for glutathione reductase and superoxide dismutase (Aono et al., Plant Cell Physiol. 36:1687, 1995), and genes for various phosphotransferases (Datta et al., Plant Mol. Biol. 20:619, 1992).

E. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282, 837; 5,767,373; and international publication WO 01/12825.

3. Genes that Confer or Contribute to a Value-Added Trait, Such as:

A. Increased iron content of the *Cannabis*, for example by transforming a plant with a soybean ferritin gene as described in Goto et al., Acta Horticulturae. 2000, 521, 101-109. Parallel to the improved iron content enhanced growth of transgenic *Cannabis* s was also observed in early development stages.

B. Decreased nitrate content of leaves, for example by transforming a *Cannabis* with a gene coding for a nitrate reductase. See for example Curtis et al., Plant Cell Report. 1999, 18: 11, 889-896.

C. Increased sweetness of the *Cannabis* by transferring a gene coding for monellin that elicits a flavor sweeter than sugar on a molar basis. See Penarrubia et al., Biotechnology. 1992, 10: 5, 561-564.

D. Modified fatty acid metabolism, for example, by transforming a plant with an antisense gene of stearyl-ACP desaturase to increase stearic acid content of the plant. See Knultzon et al., Proc. Natl. Acad. Sci. USA 89:2625 (1992).

E. Modified carbohydrate composition effected, for example, by transforming plants with a gene coding for an enzyme that alters the branching pattern of starch. See Shiroza et al., J. Bacteriol. 170:810 (1988) (nucleotide sequence of *Streptococcus* mutants fructosyltransferase gene), Steinmetz et al., Mol. Gen. Genet. 20:220 (1985) (nucleotide sequence of *Bacillus subtilis* levansucrase gene), Pen et al., Bio/Technology 10:292 (1992) (production of transgenic plants that express *Bacillus licheniformis* α-amylase), Elliot et al., Plant Molec. Biol. 21:515 (1993) (nucleotide sequences of tomato invertase genes), Sogaard et al., J. Biol. Chem. 268:22480 (1993) (site-directed mutagenesis of barley α-amylase gene), and Fisher et al., Plant Physiol. 102:1045 (1993) (maize endosperm starch branching enzyme II).

4. Genes that Control Male-Sterility

A. Introduction of a deacetylase gene under the control of a tapetum-specific promoter and with the application of the chemical N-Ac-PPT. See international publication WO 01/29237.

B. Introduction of various stamen-specific promoters. See international publications WO 92/13956 and WO 92/13957.

C. Introduction of the barnase and the barstar genes. See Paul et al., Plant Mol. Biol. 19:611-622, 1992).

Methods for *Cannabis* Transformation

Numerous methods for plant transformation have been developed, including biological and physical, plant transformation protocols. See, for example, Miki et al., "Procedures for Introducing Foreign DNA into Plants" in Methods in Plant Molecular Biology and Biotechnology, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in Methods in Plant Molecular Biology and Biotechnology, Glick B. R. and Thompson, J. E. Eds. (CRC Press, Inc., Boca Raton, 1993) pages 89-119.

A. *Agrobacterium*-Mediated Transformation

One method for introducing an expression vector into plants is based on the natural transformation system of *Agrobacterium*. See, for example, Horsch et al., Science 227:1229 (1985). Curtis et al., Journal of Experimental Botany. 1994, 45: 279, 1441-1449, Torres et al., Plant cell Tissue and Organic Culture. 1993, 34: 3, 279-285, Dinant et al., Molecular Breeding. 1997, 3: 1, 75-86. *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., Crit. Rev. Plant Sci. 10:1 (1991). Descriptions of *Agrobacterium* vector systems and methods for *Agrobacterium*-mediated gene transfer are provided by Gruber et al., supra, Miki et al., supra, and Moloney et al., Plant Cell Reports 8:238 (1989). See also, U.S. Pat. No. 5,591,616 issued Jan. 7, 1997.

B. Direct Gene Transfer

Several methods of plant transformation collectively referred to as direct gene transfer have been developed as an alternative to *Agrobacterium*-mediated transformation. A generally applicable method of plant transformation is microprojectile-mediated transformation wherein DNA is carried on the surface of microprojectiles measuring 1 to 4 µm. The expression vector is introduced into plant tissues with a biolistic device that accelerates the microprojectiles to speeds of 300 to 600 m/s which is sufficient to penetrate plant cell walls and membranes. Russell, D. R., et al. Pl. Cell. Rep. 12(3, January), 165-169 (1993), Aragao, F. J. L., et al. Plant Mol. Biol. 20(2, October), 357-359 (1992), Aragao, F. J. L., et al. Pl. Cell. Rep. 12(9, July), 483-490 (1993). Aragao, Theor. Appl. Genet. 93: 142-150 (1996), Kim, J.; Minamikawa, T. Plant Science 117: 131-138 (1996), Sanford et al., Part. Sci. Technol. 5:27 (1987), Sanford, J. C., Trends Biotech. 6:299 (1988), Klein et al., Bio/Technology 6:559-563 (1988), Sanford, J. C., Physiol Plant 7:206 (1990), Klein et al., Biotechnology 10:268 (1992).

Another method for physical delivery of DNA to plants is sonication of target cells. Zhang et al., Bio/Technology 9:996 (1991). Alternatively, liposome or spheroplast fusion has been used to introduce expression vectors into plants. Deshayes et al., EMBO J., 4:2731 (1985), Christou et al., Proc Natl. Acad. Sci. U.S.A. 84:3962 (1987). Direct uptake of DNA into protoplasts using $CaCl_2$ precipitation, polyvinyl alcohol or poly-L-omithine has also been reported. Hain et al., Mol. Gen. Genet. 199:161 (1985) and Draper et al., Plant Cell Physiol. 23:451 (1982). Electroporation of protoplasts and whole cells and tissues have also been described. Saker, M.; Kuhne, T. Biologia Plantarum 40(4): 507-514 (1997/98), Donn et al., In Abstracts of VIIth International Congress on Plant Cell and Tissue Culture IAPTC, A2-38, p 53 (1990); D'Halluin et al., Plant Cell 4:1495-1505 (1992) and Spencer et al., Plant Mol. Biol. 24:51-61 (1994). See also Chupean et al., Biotechnology. 1989, 7: 5, 503-508.

Following transformation of *Cannabis* target tissues, expression of the above-described selectable marker genes allows for preferential selection of transformed cells, tissues and/or plants, using regeneration and selection methods now well known in the art.

The foregoing methods for transformation would typically be used for producing a transgenic line. The transgenic line could then be crossed, with another (non-transformed or transformed) line, in order to produce a new transgenic *Cannabis* line. Alternatively, a genetic trait that has been engineered into a particular *Cannabis* cultivar using the foregoing transformation techniques could be moved into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

Sequence Identity

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively.

Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482-489 (1981). This algorithm can be applied to amino acid sequences by using the scoring matrix developed by Dayhoff, *Atlas of Protein Sequences and Structure*, M. O. Dayhoff ed., 5 suppl. 3:353-358, National Biomedical Research Foundation, Washington, D.C., USA, and normalized by Gribskov, *Nucl. Acids Res.* 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present disclosure is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects sequence identity. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60, expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.gov/cgi-bin/BLAST. GenBank® is the recognized United States-NIH genetic sequence database, comprising an annotated collection of publicly available DNA sequences, and which further incorporates submissions from the European Molecular Biology Laboratory (EMBL) and the DNA DataBank of Japan (DDBJ), see Nucleic Acids Research, January 2013,v 41(D1) D36-42 for discussion. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *Nucleic Acid Hybridization: A Practical Approach*, editors B. D. Hames and S. J. Higgins, (1985) Oxford; Washington, D.C.; IRL Press).

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a target molecule. Inhibition of hybridization of the completely identical sequence can be assessed using hybridization assays that are well known in the art (e.g., Southern (DNA) blot, Northern (RNA) blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule. A nucleic acid molecule that is capable of hybridizing selectively to a reference sequence under moderately stringent hybridization conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/reference sequence hybridization, where the probe and reference sequence have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

With respect to stringency conditions for hybridization, it is well known in the art that numerous equivalent conditions can be employed to establish a particular stringency by varying, for example, the following factors: the length and nature of the sequences, base composition of the various sequences, concentrations of salts and other hybridization solution components, the presence or absence of blocking agents in the hybridization solutions (e.g., dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, or preferably at least 70%, 80%, 90%, and most preferably at least 95%.

Another indication that nucleotide sequences are substantially identical is if two molecules hybridize to each other under stringent conditions. However, nucleic acids which do not hybridize to each other under stringent conditions are still substantially identical if the polypeptides which they encode are substantially identical. This may occur, e.g., when a copy of a nucleic acid is created using the maximum codon degeneracy permitted by the genetic code. One indication that two nucleic acid sequences are substantially identical is that the polypeptide which the first nucleic acid encodes is immunologically cross reactive with the polypeptide encoded by the second nucleic acid.

The term "conservatively modified variants" applies to both amino acid and nucleic acid sequences. With respect to particular nucleic acid sequences, conservatively modified variants refer to those nucleic acids which encode identical or conservatively modified variants of the amino acid sequences. Because of the degeneracy of the genetic code, a large number of functionally identical nucleic acids encode any given protein, for instance, the codons GCA, GCC, GCG, and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W.H. Freeman and Company.

By "encoding" or "encoded," with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum* (Yamao, et al., (1985) Proc. Natl. Acad. Sci. USA 82:2306-9), or the ciliate Macronucleus, may be used when the nucleic acid is expressed using these organisms.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledonous plants or dicotyledonous plants as these preferences have been shown to differ (Murray, et al., (1989) Nucleic Acids Res. 17:477-98 and herein incorporated by reference). Thus, the maize preferred codon for a particular amino acid might be derived from known gene sequences from maize. Maize codon usage for 28 genes from maize plants is listed in Table 4 of Murray, et al., supra.

Tilling

In one embodiment, TILLING (Targeting Induced Local Lesions IN Genomes) can be used to produce plants in which endogenous genes comprise a mutation, for example genes increase female gender skew. In a first step, introduced mutations such as novel single base pair changes are induced in a population of plants by treating seeds (or pollen) with a chemical mutagen, and then advancing plants to a generation where mutations will be stably inherited. DNA is extracted, and seeds are stored from all members of the population to create a resource that can be accessed repeatedly over time. For a TILLING assay, heteroduplex methods using specific endonucleases can be used to detect single nucleotide polymorphisms (SNPs). Alternatively, Next Generation Sequencing of DNA from pools of mutagenized plants can be used to identify mutants in the gene of choice. Typically, a mutation frequency of one mutant per 1000 plants in the mutagenized population is achieved. Using this approach, many thousands of plants can be screened to identify any individual with a single base change as well as small insertions or deletions (1-30 bp) in any gene or specific region of the genome. TILLING is further described in Slade and Knauf (2005), and Henikoff et al. (2004).

In addition to allowing efficient detection of mutations, high-throughput TILLING technology is ideal for the detection of natural polymorphisms. Therefore, interrogating an unknown homologous DNA by heteroduplexing to a known sequence reveals the number and position of polymorphic sites. Both nucleotide changes and small insertions and deletions are identified, including at least some repeat number polymorphisms. This has been called Ecotilling (Comai et al., 2004).

Genome Editing Using Site-Specific Nucleases

Genome editing uses engineered nucleases such as RNA guided DNA endonucleases or nucleases composed of sequence specific DNA binding domains fused to a non-specific DNA cleavage module. These engineered nucleases enable efficient and precise genetic modifications by inducing targeted DNA double stranded breaks that stimulate the cell's endogenous cellular DNA repair mechanisms to repair the induced break. Such mechanisms include, for example, error prone non-homologous end joining (NHEJ) and homology directed repair (HDR).

In the presence of donor plasmid with extended homology arms, HDR can lead to the introduction of single or multiple transgenes to correct or replace existing genes. In the absence of donor plasmid, NHEJ-mediated repair yields small insertion or deletion mutations of the target that cause gene disruption. Engineered nucleases useful in the methods of the present invention include zinc finger nucleases (ZFNs), transcription activator-like (TAL) effector nucleases (TALEN) and CRISPR/Cas9 type nucleases.

Typically, nuclease encoded genes are delivered into cells by plasmid DNA, viral vectors or in vitro transcribed mRNA. A zinc finger nuclease (ZFN) comprises a DNA-binding domain and a DNA-cleavage domain, wherein the DNA binding domain is comprised of at least one zinc finger and is operatively linked to a DNA-cleavage domain. The zinc finger DNA-binding domain is at the N-terminus of the protein and the DNA-cleavage domain is located at the C-terminus of said protein.

A ZFN must have at least one zinc finger. In a preferred embodiment, a ZFN would have at least three zinc fingers in order to have sufficient specificity to be useful for targeted genetic recombination in a host cell or organism. Typically, a ZFN having more than three zinc fingers would have progressively greater specificity with each additional zinc finger.

The zinc finger domain can be derived from any class or type of zinc finger. In a particular embodiment, the zinc finger domain comprises the Cis2His2 type of zinc finger that is very generally represented, for example, by the zinc finger transcription factors TFIIIA or Sp1. In a preferred embodiment, the zinc finger domain comprises three Cis2His2 type zinc fingers. The DNA recognition and/or the binding specificity of a ZFN can be altered in order to accomplish targeted genetic recombination at any chosen site in cellular DNA. Such modification can be accomplished using known molecular biology and/or chemical synthesis techniques (see, for example, Bibikova et al., 2002).

The ZFN DNA-cleavage domain is derived from a class of non-specific DNA cleavage domains, for example the DNA-cleavage domain of a Type II restriction enzyme such as FokI (Kim et al., 1996). Other useful endonucleases may include, for example, HhaI, HindIII, Nod, BbvCI, EcoRI, BglI, and AlwI.

A transcription activator-like (TAL) effector nuclease (TALEN) comprises a TAL effector DNA binding domain and an endonuclease domain. TAL effectors are proteins of plant pathogenic bacteria that are injected by the pathogen into the plant cell, where they travel to the nucleus and function as transcription factors to turn on specific plant genes. The primary amino acid sequence of a TAL effector dictates the nucleotide sequence to which it binds. Thus, target sites can be predicted for TAL effectors, and TAL effectors can be engineered and generated for the purpose of binding to particular nucleotide sequences.

Fused to the TAL effector-encoding nucleic acid sequences are sequences encoding a nuclease or a portion of a nuclease, typically a nonspecific cleavage domain from a type II restriction endonuclease such as FokI (Kim et al., 1996). Other useful endonucleases may include, for example, HhaI, HindIII, Nod, BbvCI, EcoRI, BglI, and AhvI. The fact that some endonucleases (e.g., FokI) only function as dimers can be capitalized upon to enhance the target specificity of the TAL effector. For example, in some cases each FokI monomer can be fused to a TAL effector sequence that recognizes a different DNA target sequence, and only when the two recognition sites are in close proximity do the inactive monomers come together to create a functional enzyme. By requiring DNA binding to activate the nuclease, a highly site-specific restriction enzyme can be created.

A sequence-specific TALEN can recognize a particular sequence within a preselected target nucleotide sequence present in a cell. Thus, in some embodiments, a target nucleotide sequence can be scanned for nuclease recognition sites, and a particular nuclease can be selected based on the target sequence. In other cases, a TALEN can be engineered to target a particular cellular sequence.

Genome Editing Using Programmable RNA-Guided DNA Endonucleases

Distinct from the site-specific nucleases described above, the clustered regulatory interspaced short palindromic repeats (CRISPR)/Cas system provides an alternative to ZFNs and TALENs for inducing targeted genetic alterations, via RNA-guided DNA cleavage.

CRISPR systems rely on CRISPR RNA (crRNA) and transactivating chimeric RNA (tracrRNA) for sequence-specific cleavage of DNA. Three types of CRISPR/Cas systems exist: in type II systems, Cas9 serves as an RNA-guided DNA endonuclease that cleaves DNA upon crRNA-tracrRNA target recognition. CRISPR RNA base pairs with tracrRNA to form a two-RNA structure that guides the Cas9 endonuclease to complementary DNA sites for cleavage.

The CRISPR system can be portable to plant cells by co-delivery of plasmids expressing the Cas endonuclease and the necessary crRNA components. The Cas endonuclease may be converted into a nickase to provide additional control over the mechanism of DNA repair (Cong et al., 2013). CRISPRs are typically short partially palindromic sequences of 24-40 bp containing inner and terminal inverted repeats of up to 11 bp. Although isolated elements have been detected, they are generally arranged in clusters (up to about 20 or more per genome) of repeated units spaced by unique intervening 20-58 bp sequences. CRISPRs are generally homogenous within a given genome with most of them being identical. However, there are examples of heterogeneity in, for example, the Archaea (Mojica et al., 2000).

Gene Conversions

When the term *Cannabis* plant, cultivar or *Cannabis* line is used in the context of the present invention, this also includes any gene conversions of that line. The term gene converted plant as used herein refers to those *Cannabis* plants which are developed by a plant breeding technique called backcrossing wherein essentially all of the desired morphological and physiological characteristics of a cultivar are recovered in addition to the gene transferred into the line via the backcrossing technique. Backcrossing methods can be used with the present invention to improve or introduce a characteristic into the line. The term backcrossing as used herein refers to the repeated crossing of a hybrid progeny back to one of the parental *Cannabis* plants for that line. The parental *Cannabis* plant that contributes the gene for the desired characteristic is termed the nonrecurrent or donor parent. This terminology refers to the fact that the nonrecurrent parent is used one time in the backcross protocol and therefore does not recur. The parental *Cannabis* plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original cultivar of interest (recurrent parent) is crossed to a second line (nonrecurrent parent) that carries the single gene of interest to be transferred. The resulting progeny from this cross are then crossed again to the recurrent parent and the process is repeated until a *Cannabis* plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute traits or characteristics in the original line. To accomplish this, a gene or genes of the recurrent cultivar are modified or substituted with the desired gene or genes from the nonrecurrent parent, while retaining essentially all of the rest of the desired genetic, and therefore the desired physiological and morphological, constitution of the original line. The choice of the particular nonrecurrent parent will depend on the purpose of the backcross. One of the major purposes is to add some commercially desirable, agronomically important trait or traits to the plant. The exact backcrossing protocol will depend on the characteristics or traits being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many gene traits have been identified that are not regularly selected for in the development of a new line but that can be improved by backcrossing techniques. Gene traits may or may not be transgenic, examples of these traits include but are not limited to, herbicide resistance, resistance for bacterial, fungal, or viral disease, insect resistance, enhanced nutritional quality, industrial usage, yield stability, yield enhancement, male sterility, modified fatty acid metabolism, and modified carbohydrate metabolism. These genes are generally inherited through the nucleus. Several of these gene traits are described in U.S. Pat. Nos. 5,777,196; 5,948,957 and 5,969,212, the disclosures of which are specifically hereby incorporated by reference.

Tissue Culture

Further reproduction of the variety can occur by tissue culture and regeneration. Tissue culture of various tissues of *Cannabis* and regeneration of plants therefrom is well known and widely published. For example, reference may be had to Teng et al., HortScience. 1992, 27: 9, 1030-1032 Teng et al., HortScience. 1993, 28: 6, 669-1671, Zhang et al., Journal of Genetics and Breeding. 1992, 46: 3, 287-290, Webb et al., Plant Cell Tissue and Organ Culture. 1994, 38: 1, 77-79, Curtis et al., Journal of Experimental Botany.

1994, 45: 279, 1441-1449, Nagata et al., Journal for the American Society for Horticultural Science. 2000, 125: 6, 669-672, and Ibrahim et al., Plant Cell, Tissue and Organ Culture. (1992), 28(2): 139-145. It is clear from the literature that the state of the art is such that these methods of obtaining plants are routinely used and have a very high rate of success. Thus, another aspect of this invention is to provide cells which upon growth and differentiation produce *Cannabis* plants having the physiological and morphological characteristics of cultivar NWG28.

As used herein, the term "tissue culture" indicates a composition comprising isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques, the disclosures of which are incorporated herein by reference.

Additional Breeding Methods

This invention also is directed to methods for producing a *Cannabis* plant by crossing a first parent *Cannabis* plant with a second parent *Cannabis* plant wherein the first or second parent *Cannabis* plant is a *Cannabis* plant of cultivar NWG28. Further, both first and second parent *Cannabis* plants can come from hemp *Cannabis* cultivar NWG28. Thus, any such methods using hemp *Cannabis* cultivar NWG28 are part of this invention: selfing, backcrosses, hybrid production, crosses to populations, and the like. All plants produced using hemp *Cannabis* cultivar NWG28 as at least one parent are within the scope of this invention, including those developed from cultivars derived from hemp *Cannabis* cultivar NWG28. Advantageously, this *Cannabis* cultivar could be used in crosses with other, different, *Cannabis* plants to produce the first generation (F₁) *Cannabis* hybrid seeds and plants with superior characteristics. The cultivar of the invention can also be used for transformation where exogenous genes are introduced and expressed by the cultivar of the invention. Genetic variants created either through traditional breeding methods using hemp *Cannabis* cultivar NWG28 or through transformation of cultivar NWG28 by any of a number of protocols known to those of skill in the art are intended to be within the scope of this invention.

The following describes breeding methods that may be used with the hemp *Cannabis* cultivar of the invention in the development of further *Cannabis* plants. One such embodiment is a method for developing cultivar NWG28 progeny *Cannabis* plants in a *Cannabis* plant breeding program comprising: obtaining the *Cannabis* plant, or a part thereof, of cultivar NWG28, utilizing said plant or plant part as a source of breeding material, and selecting a hemp *Cannabis* cultivar of the invention progeny plant with molecular markers in common with cultivar NWG28 and/or with morphological and/or physiological characteristics selected from the characteristics listed in Table 1. Breeding steps that may be used in the *Cannabis* plant breeding program include pedigree breeding, backcrossing, mutation breeding, and recurrent selection. In conjunction with these steps, techniques such as RFLP-enhanced selection, genetic marker enhanced selection (for example SSR markers) and the making of double haploids may be utilized.

Another method which may be used involves producing a population of hemp *Cannabis* cultivar NWG28-progeny *Cannabis* plants, comprising crossing cultivar NWG28 with another *Cannabis* plant, thereby producing a population of *Cannabis* plants, which, on average, derive 50% of their alleles from hemp *Cannabis* cultivar NWG28. A plant of this population may be selected and repeatedly selfed or sibbed with a *Cannabis* cultivar resulting from these successive filial generations. One embodiment of this invention is the *Cannabis* cultivar produced by this method and that has obtained at least 50% of its alleles from hemp *Cannabis* cultivar NWG28.

One of ordinary skill in the art of plant breeding would know how to evaluate the traits of two plant varieties to determine if there is no significant difference between the two traits expressed by those varieties. For example, see Fehr and Walt, Principles of Cultivar Development, p 261-286 (1987). Thus the invention includes hemp *Cannabis* cultivar NWG28 progeny *Cannabis* plants comprising a combination of at least two cultivar NWG28 traits selected from the group consisting of those listed in Table 1 or the cultivar NWG28 combination of traits listed above, so that said progeny *Cannabis* plant is not significantly different for said traits than hemp *Cannabis* cultivar NWG28 as determined at the 5% significance level when grown in the same environmental conditions. Using techniques described herein, molecular markers may be used to identify said progeny plant as a hemp *Cannabis* cultivar NWG28 progeny plant. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

Progeny of hemp *Cannabis* cultivar NWG28 may also be characterized through their filial relationship with hemp *Cannabis* cultivar NWG28, as for example, being within a certain number of breeding crosses of hemp *Cannabis* cultivar NWG28. A breeding cross is a cross made to introduce new genetics into the progeny, and is distinguished from a cross, such as a self or a sib cross, made to select among existing genetic alleles. The lower the number of breeding crosses in the pedigree, the closer the relationship between hemp *Cannabis* cultivar NWG28 and its progeny. For example, progeny produced by the methods described herein may be within 1, 2, 3, 4 or 5 breeding crosses of hemp *Cannabis* cultivar NWG28.

The foregoing invention has been described in detail by way of illustration and example for purposes of clarity and understanding. However, it will be obvious that certain changes and modifications such as single gene modifications and mutations, somaclonal variants, variant individuals selected from large populations of the plants of the instant variety and the like may be practiced within the scope of the invention, as limited only by the scope of the appended claims.

EXAMPLES

Example 1: *Cannabis* NWG28

A variety description of *Cannabis* Cultivar NWG28 is provided in Table 1.

TABLE 1

Variety Description Information

| Trait | |
|---|---|
| Cotyledon shape | Narrow obvate |
| Cotyledon color | Medium green |
| Hypocotyl: intensity of anthocyanin coloration | Weak |
| Plant: anthocyanin coloration of crown | Absent |
| Leaf: intensity of green color | Medium |
| Leaf: length of petiole | Medium |
| Leaf: anthocyanin coloration of petiole | Absent |
| Leaf: number of leaflets | Seven |
| Leaf: central leaflet length | Medium |
| Leaf: central leaflet width | Medium |
| Time of Male Flowering | Medium (60 days) |
| Inflorescence: anthocyanin coloration of male flowers | Weak |
| Inflorescence: THC content | Absent or very low |
| Plant: proportion of hermaphrodite plants | Medium |
| Plant: proportion of female plants | Medium |
| Plant: proportion of male plants | Low to medium |
| Plant: natural height | Medium |
| Main stem: color | Medium green |
| Main stem: length of internode | Medium |
| Main stem: thickness | Thin |
| Main stem: depth of grooves | Shallow |
| Main stem: pith in cross section | Medium |
| Seed: 1,000 seed weight | 12.4 grams (Rep 1) |
|  | 12.7 grams (Rep 2) |
| Seed: color of testa | Grey brown |
| Seed: marbling | Medium |

A single, monoecious industrial hemp plant known as NWG28 was used in crossing with a randomly selected female from a heterogeneous breeding population. The plants were bagged together to ensure the seed produced on the female were the progeny of NWG28. The resulting population demonstrated a ratio of females near 90%.

The seed harvested from the bagged NWG28 used in crossing was planted in a greenhouse along with 24 breeding populations. Approximately 30 plants of each genotype were grown until flowering at which point males were destroyed for all genotypes and only monoecious plants from NWG28 were kept as pollen sources for crossing with females from all other populations. The details of the genotypes used in this crossing matrix and subsequent yields are outlined in Table 2.

TABLE 2

Female ID, Male ID and yield (in grams) of greenhouse testcrosses.

| Female NWG ID | Male NWG ID | seed mass (g) |
|---|---|---|
| NWG11-1 | NWG28 | 3 |
| NWG11-7 | NWG28 | 5 |
| NWG11-8 | NWG28 | 2.8 |
| NWG201 | NWG28 | 9.2 |
| NWG238 | NWG28 | 5.1 |
| NWG239 | NWG28 | 3.3 |
| NWG240 | NWG28 | 11.3 |
| NWG242 | NWG28 | 6.4 |
| NWG260 | NWG28 | 8 |
| NWG274 | NWG28 | 1.8 |
| NWG28 | NWG28 | 12 |
| NWG296 | NWG28 | 4.4 |
| NWG328 | NWG28 | 3.1 |
| NWG364 | NWG28 | 5.6 |
| NWG37 | NWG28 | 1.9 |
| NWG372 | NWG28 | 9.75 |
| NWG373 | NWG28 | 6.7 |
| NWG60 | NWG28 | 8.8 |
| NWG369 | NWG28 | 29.9 |

Progeny of these crosses were planted in 2 m rows in the field and grown to flowering at which point the sex ratio of the population was determined by evaluating the sex of each plant by eye. Hermaphrodites were scored as males although these were rare. The results shown in Table 3 demonstrate that the progeny of NWG28 generally have a higher frequency of females than would be expected by chance based on a chi-square test and that this frequency can be as high as 92% (Population 19). Interestingly, some populations resulted in ratios skewed in favor of male plants. Examples include Populations 8 and 11.

TABLE 3

Number of females, males, percentage of females and P-value for Chi-Square tests of deviation from the expected ratio of 50% females.

| Population | Females | Males | % Females | P-value |
|---|---|---|---|---|
| 1* | 20 | 9 | 69.0% | 0.041 |
| 2* | 25 | 10 | 71.4% | 0.011 |
| 3* | 20 | 7 | 74.1% | 0.012 |
| 4* | 33 | 7 | 82.5% | 0.000 |
| 5* | 27 | 12 | 69.2% | 0.016 |
| 6 | 18 | 10 | 64.3% | 0.131 |
| 7* | 24 | 8 | 75.0% | 0.005 |
| 8 | 12 | 18 | 40.0% | 0.273 |
| 9 | 10 | 5 | 66.7% | 0.197 |
| 10 | 5 | 3 | 62.5% | 0.480 |
| 11 | 11 | 13 | 45.8% | 0.683 |
| 12* | 22 | 8 | 73.3% | 0.011 |
| 13 | 14 | 7 | 66.7% | 0.127 |
| 14* | 26 | 3 | 89.7% | 0.000 |
| 15* | 20 | 2 | 90.9% | 0.000 |
| 16 | 7 | 6 | 53.8% | 0.782 |
| 17* | 16 | 4 | 80.0% | 0.007 |
| 18 | 25 | 16 | 61.0% | 0.160 |
| 19* | 35 | 3 | 92.1% | 0.000 |
| 20 | 3 | 1 | 75.0% | 0.317 |
| Total* | 373 | 152 | 71.0% | 0.000 |

*Indicates populations with significantly skewed ratios at P = 0.05

Table 4 shows typical cannabinoid content estimates as determined by High-performance liquid chromatography (% dry wt) in female bud tissue harvested from NWG28.

TABLE 4

Typical cannabinoid content estimates.

| THC | THC-A | CBD | CBD-A | CBN | CBG | Total |
|---|---|---|---|---|---|---|
| 0.00% | 0.00% | 0.43% | 2.93% | 0.00% | 0.00% | 3.36% |
| 0.00% | 0.00% | 0.47% | 3.05% | 0.00% | 0.00% | 3.52% |
| 0.00% | 0.00% | 0.48% | 2.84% | 0.00% | 0.00% | 3.32% |

Example 2: Genome Mapping for Markers) Associated with Greater than 50% Females in *Cannabis sativa*

Experimental Design

Mapping population—All of the following work was conducted in greenhouses to control environmental variation. Individuals from populations 11 and 16 of Table 3 were self-pollinated for one generation by pairing one male plant with one female plant under a selfing bag. Three such pairs were harvested from population 11, and four were harvested from population 16. In the next generation, male progeny from these self-pollinated plants were paired with females from NWG1270 (an inbred line) under selfing bags. Leaf tissue was collected from each male for DNA extraction. Finally, progeny populations from each of these crosses were grown until anthesis at which time the sex of each plant was recorded.

Genotyping—DNA was extracted from leaf tissue collected from the sires of the crosses using a standard DNA extraction kit. Extracted DNA was sent to Freedom Markers (Ames, Iowa) for genotyping-by-sequencing using their tGBS technology conducted with the restriction enzyme Bsp1286I. Reads were aligned to the *Cannabis sativa* GCA 003417725.2 reference genome. A total of 335,901 SNP sites were genotyped in at least 50% of the samples where each SNP is supported on average by 58 tGBS reads/SNP/genotyped sample.

Mapping—A genome-wide association study (GWAS) was used to scan for marker-trait associations. Genotype data was filtered to remove SNPs not assigned to the 10 pseudo-molecules of the draft *Cannabis sativa* genome, monomorphic sites and those with minor allele frequencies less than 0.05. This left 153,687 SNPs which were used to conduct a genome-wide scan in TASSEL (Bradbury P J, Zhang Z, Kroon D E, Casstevens T M, Ramdoss Y, Buckler E S. (2007) TASSEL: Software for association mapping of complex traits in diverse samples. Bioinformatics 23:2633-2635) using the general linear model (GLM).

Results

A cluster of three linked SNPs on chromosome 4 (a.k.a. CM011608.1) were found to be significantly associated with a ratio of female plants to male plants greater than 1:1 after correcting the p-value for the multiple comparisons of the genome-wide scan (Table 5).

TABLE 5

Pseudomolecule name, chromosome, physical position, p-value, genotype and mean ratio of females to males for markers significantly associated with a greater than 1:1 ratio of females to males (F:M).

| rs# | chrom | pos | GWAS p-value | Genotype | Mean ratio | Genotype | Mean ratio |
|---|---|---|---|---|---|---|---|
| CM011608.1 | 4 | 43581285 | 3.21E−07 | GA | 2.10 | GG | 1.13 |
| CM011608.1 | 4 | 43581290 | 3.21E−07 | CT | 2.10 | CC | 1.13 |
| CM011608.1 | 4 | 43581292 | 3.21E−07 | GA | 2.10 | GG | 1.13 |

* P-value corrected for genome-wide multiple comparisons = 3.253E−07

TABLE 6

Polymorphic loci in brackets and flanking DNA of the haplotype associated with gender skew on chromosome CM011608.1 (chromosome 4: position 43581235-43581334) of reference CA_003417725.2 (SEQ ID NO: 1).

CAAGCATGTTTGCTCCAATGGTAATGGTTTTCAGCGTGATTATACATTTT
[G/A]TAAC[C/T]T[G/A]CAGCAATCATATATTTATTATTGATAAAGA
TAGCAGGATCAA

Sequences
>SEQ ID NO: 2 (Reference)
CAAGCATGTTTGCTCCAATGGTAATGGTTTTCAGCGTGATTATACATTTT
GTAACCTGCAGCAATCATATATTTATTATTGATAAAGATAGCAGGATCAA >SEQ ID NO: 3 (43581285)
CAAGCATGTTTGCTCCAATGGTAATGGTTTTCAGCGTGATTATACATTTT
ATAACCTGCAGCAATCATATATTTATTATTGATAAAGATAGCAGGATCAA >SEQ ID NO: 4 (43581290)
CAAGCATGTTTGCTCCAATGGTAATGGTTTTCAGCGTGATTATACATTTT
GTAACTTGCAGCAATCATATATTTATTATTGATAAAGATAGCAGGATCAA >SEQ ID NO: 5 (43581292)
CAAGCATGTTTGCTCCAATGGTAATGGTTTTCAGCGTGATTATACATTTT
GTAACCTACAGCAATCATATATTTATTATTGATAAAGATAGCAGGATCAA

What is claimed is:

1. A method of identifying a *Cannabis* plant comprising at least one allele associated with female gender skew in a *Cannabis* plant comprising:
   a) isolating DNA from at least one *Cannabis* plant;
   b) detecting in said isolated DNA one or more nucleic acid markers, wherein said one or more nucleic acid markers is selected from SEQ ID NOs: 3, 4, or 5; and
   c) selecting based upon said detecting at least one *Cannabis* plant comprising an allele of at least one of said one or more nucleic acid markers that is associated with female gender skew, wherein the allele comprises an 'A' at position 51 of SEQ ID NO: 3, a 'T' at position 56 of SEQ ID NO: 4, or an 'A' at position 58 of SEQ ID NO: 5.

2. The method of claim 1, further comprising the step of crossing the *Cannabis* plant selected in step (c) with another *Cannabis* plant.

3. The method of claim 1, further comprising the step of obtaining seed from the *Cannabis* plant selected in step (c).

4. A method of creating a population of *Cannabis* plants each comprising at least one allele associated with female gender skew, the method comprising the steps of:

a) isolating DNA from at least one *Cannabis* plant;
   b) detecting in said isolated DNA one or more nucleic acid markers, wherein said one or more nucleic acid markers is selected from SEQ ID NOs: 3, 4, or 5;
   c) selecting based upon said detecting at least one *Cannabis* plant comprising an allele of at least one of said one or more nucleic acid markers that is associated with female gender skew, wherein the allele comprises an 'A' at position 51 of SEQ ID NO: 3, a 'T' at position 56 of SEQ ID NO: 4, or an 'A' at position 58 of SEQ ID NO: 5; and
   d) crossing the at least one *Cannabis* plant selected in step (c) with at least one second *Cannabis* plant to produce a population of *Cannabis* plants each comprising said at least one allele associated with female gender skew.

5. The method of claim 4, wherein said crossing in step (d) comprises crossing the one or more selected *Cannabis* plants with a second *Cannabis* plant, wherein said second *Cannabis* plant has no gender skew.

* * * * *

SEQUENCE LISTING

<160> NUMBER OF SEQ ID NOS: 5

<210> SEQ ID NO 1
<211> LENGTH: 100
<212> TYPE: DNA
<213> ORGANISM: Cannabis sativa

<400> SEQUENCE: 1
caagcatgtt tgctccaatg gtaatggttt tcagcgtgat tatacatttt rtaacytrca        60
gcaatcatat atttattatt gataaagata gcaggatcaa                              100

```
<210> SEQ ID NO 2
<211> LENGTH: 100
<212> TYPE: DNA
<213> ORGANISM: Cannabis sativa

<400> SEQUENCE: 2
caagcatgtt tgctccaatg gtaatggttt tcagcgtgat tatacatttt gtaacctgca        60
gcaatcatat atttattatt gataaagata gcaggatcaa                            100

<210> SEQ ID NO 3
<211> LENGTH: 100
<212> TYPE: DNA
<213> ORGANISM: Cannabis sativa

<400> SEQUENCE: 3
caagcatgtt tgctccaatg gtaatggttt tcagcgtgat tatacatttt ataacctgca        60
gcaatcatat atttattatt gataaagata gcaggatcaa                            100

<210> SEQ ID NO 4
<211> LENGTH: 100
<212> TYPE: DNA
<213> ORGANISM: Cannabis sativa

<400> SEQUENCE: 4
caagcatgtt tgctccaatg gtaatggttt tcagcgtgat tatacatttt gtaacttgca        60
gcaatcatat atttattatt gataaagata gcaggatcaa                            100

<210> SEQ ID NO 5
<211> LENGTH: 100
<212> TYPE: DNA
<213> ORGANISM: Cannabis sativa

<400> SEQUENCE: 5
caagcatgtt tgctccaatg gtaatggttt tcagcgtgat tatacatttt gtaacctaca        60
gcaatcatat atttattatt gataaagata gcaggatcaa                            100
```